United States Patent
Senda et al.

(10) Patent No.: US 7,851,569 B2
(45) Date of Patent: Dec. 14, 2010

(54) RARE EARTH METAL COMPLEX, POLYMERIZATION CATALYST, AND PROCESS FOR PRODUCING POLYMER

(75) Inventors: Taichi Senda, Takatsuki (JP); Hidenori Hanaoka, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 130 days.

(21) Appl. No.: 12/309,082

(22) PCT Filed: Jul. 5, 2007

(86) PCT No.: PCT/JP2007/063484

§ 371 (c)(1),
(2), (4) Date: Jan. 6, 2009

(87) PCT Pub. No.: WO2008/004628

PCT Pub. Date: Jan. 10, 2008

(65) Prior Publication Data

US 2009/0253875 A1    Oct. 8, 2009

(30) Foreign Application Priority Data

Jul. 7, 2006 (JP) .............................. 2006-187607
Feb. 20, 2007 (JP) .............................. 2007-039071

(51) Int. Cl.
C08F 4/52 (2006.01)
C07F 17/00 (2006.01)
C07F 5/00 (2006.01)
B01J 31/22 (2006.01)

(52) U.S. Cl. ................. 526/160; 526/133; 526/134; 526/165; 526/319; 526/348; 526/943; 502/103; 502/152; 502/156; 556/1; 556/11

(58) Field of Classification Search ............ 556/1, 556/11; 502/103, 152, 156; 526/133, 134, 526/160, 165, 319, 348, 943
See application file for complete search history.

(56) References Cited

U.S. PATENT DOCUMENTS

| 5,028,667 | A | 7/1991 | McLain et al. |
| 6,329,478 | B1 | 12/2001 | Katayama et al. |
| 6,548,686 | B2 * | 4/2003 | Nabika et al. ............. 556/51 |
| 2002/0058585 | A1 | 5/2002 | Christopher et al. |
| 2007/0232758 | A1 | 10/2007 | Hou et al. |

FOREIGN PATENT DOCUMENTS

| JP | 05-247184 A | 9/1993 |
| JP | 06-263783 A | 9/1994 |
| JP | 09-087313 A | 3/1997 |
| JP | 2003-327594 A | 11/2003 |
| JP | 2004-204145 A | 7/2004 |
| JP | 2005-002072 A | 1/2005 |
| WO | WO 91/05001 A1 | 4/1991 |
| WO | WO 00/18808 A1 | 4/2000 |
| WO | WO 2006/004068 A1 | 1/2006 |

OTHER PUBLICATIONS

Cui et al., "Alternating Copolymerization of Cyclohexene Oxide and Carbon Dioxide Catalyzed by Organo Rare Earth Metal Complexes," Macromolecules, 2005, 38:4089-4095.
Tanaka et al., "Unique Dual Function of La(C5Me5)[CH(SiMe3)2]2(THF) for Polymerizations of Both Nonpolar and Polar Monomers," Journal of Polymer Science, Part A: Polymer Chemistry, 2001, 39:1382-1390.
Yamashita et al., "Organolanthanide-Initiated Living Polymerizations of ε-Caprolactine, δ-Valerolactone, and β-Propiolactone," Macromolecules, 1996, 29:1798-1806.

* cited by examiner

*Primary Examiner*—Caixia Lu
(74) *Attorney, Agent, or Firm*—Foley & Lardner LLP

(57) ABSTRACT

A rare earth metal complex represented by the formula (1):

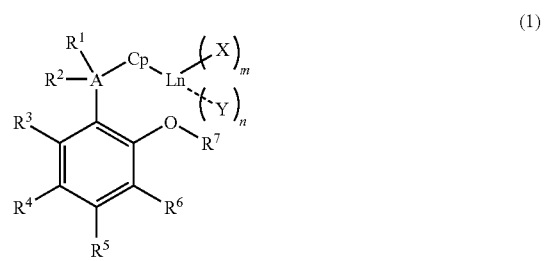

in which A represents a Group 14 element of the periodic table, Cp represents a group having a substituted or unsubstituted cyclopentadienyl anion moiety, Ln represents a Group 3 metal atom or a lanthanoid metal atom, $R^1$ to $R_6$ are the same or different, and represent a hydrogen atom, a halogen atom, an alkyl group having 1 to 20 carbon atoms, an aryl group having 6 to 20 carbon atoms, an aralkyl group having 7 to 20 carbon atoms, a silyl group substituted with a hydrocarbon group having 1 to 20 carbon atoms, an alkoxy group having 1 to 20 carbon atoms, $R^7$ represents an alkyl group having 1 to 20 carbon atoms, an aryl group having 6 to 20 carbon atoms, or an aralkyl group having 7 to 20 carbon atoms, Xs represent a monoanionic ligand, Ys represent a neutral ligand, m represents an integer of 1 to 3, and n represents an integer of 0 to 3. The rare earth metal complex is useful as, for example, a catalyst for polymerization reaction of olefins. A polar monomer such as a lactone can be polymerized using the rare earth metal complex as a catalyst.

12 Claims, No Drawings

RARE EARTH METAL COMPLEX, POLYMERIZATION CATALYST, AND PROCESS FOR PRODUCING POLYMER

CROSS-REFERENCE TO RELATED APPLICATIONS

This application is a National Stage application of PCT/JP2007/063484, filed Jul. 5, 2007, which claims priority from Japanese applications JP 2006-187607, filed Jul. 7, 2006, and JP 2007-039071, filed Feb. 20, 2007.

FIELD OF THE INVENTION

The present invention relates to a rare earth metal complex and a process for producing the same, a catalyst for olefin or lactone polymerization containing the rate earth metal complex, as well as a process for producing a polymer of an olefin or of a polar monomer such as a lactone.

BACKGROUND ART

A metallocene complex having one cyclopentadiene ligand is a compound which is called a half metallocene complex and utilized as a catalytic component for polymerizing various olefins, and it is known that the property thereof (a catalytic activity on a polymerization reaction) greatly varies depending on the kind of its central metal. Inter alia, it is known that a polymerization catalytic component comprising a half metallocene complex having a Group 3 metal or a lanthanoid metal (hereinafter, a Group 3 metal and a lanthanoid metal are collectively referred to as rare earth metals) as a central metal can be used in the polymerization or copolymerization of ethylene and α-olefins, the polymerization or copolymerization of aromatic olefin monomers such as styrene, and the polymerization or copolymerization of cyclic olefin monomers such as norbornene (see WO 2006/004068). It is also known that such a half metallocene complex having a rare earth metal as a central metal can be used in the polymerization of cyclohexene oxide, and the copolymerization of cyclohexene oxide and carbon dioxide (see Macromolecules 2005, 38, 4089). It is known that a half metallocene complex having lanthanum as a central metal can be used in the syndiotactic polymerization of a methacrylate ester, the block copolymerization of ethylene and a methacrylate ester, the polymerization of isocyanide, and the polymerization of acrylonitrile (see J. Polym. Sci.: Part A: Polym. Chem. 2001, 39, 1382). Thus, the half metallocene complex having a rare earth metal as a central metal is a useful metal complex for which many utilities are expected. On the other hand, as a metal complex having a ligand in which a cyclopentadiene derivative and a phenol derivative are linked with a Group 14 atom, a Group 4 transition metal complex is known as a catalyst for olefin polymerization (see JP-A-09-87313), but no rare earth metal complex is known.

The polymers of lactone compounds such as ε-caprolactone which can be industrially produced at low cost are useful as modifiers for polyurethane, coating resins and plastics. Among those polymers, particularly the lactone polymer with a high molecular weight attracts attention as a biodegradable polymer. As a process for producing the high-molecular weight polymer of a lactone, a method of ring-opening polymerization of a lactone using a rare earth alkoxide as a catalyst (see WO 91/05001), or a method of ring-opening polymerization of a lactone using a rare earth complex having a cyclopentadiene ligand as a catalyst is known (see JP-A-05-247184). After that, regarding the ring-opening polymerization of a lactone using a rare earth complex as a catalyst, efforts for efficiently obtaining a polymer having a narrow molecular weight distribution have been reported (see Macromolecules, 1996, 29, 1798).

SUMMARY OF THE INVENTION

Problems to be Solved by the Invention

The first object of the present invention is to provide a novel rare earth metal complex which can be utilized as a catalytic component for polymerizing an olefin or a polar monomer such as a lactone, and a process for producing the same.

The second object of the present invention is to provide a process for producing a polymer or a copolymer of an olefin using such a catalytic component comprising a rare earth metal complex.

The third object of the present invention is to provide a process for producing a polymer of a polar monomer using such a catalytic component comprising a rare earth metal complex, inter alia, a process for efficiently producing a high-molecular weight polymer of a lactone.

Means for Solving the Problems

According to the first aspect, the present invention provides a rare earth metal complex represented by the formula (1):

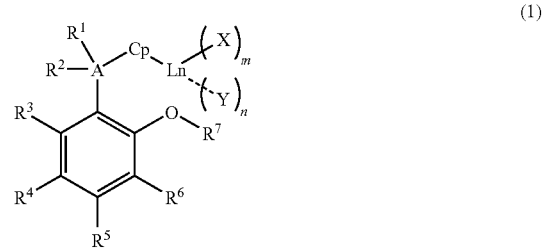

wherein
A represents a Group 14 element of the periodic table,
Cp represents a group having a substituted or unsubstituted cyclopentadienyl anion moiety,
Ln represents a Group 3 metal atom or a lanthanoid metal atom,
$R^1$, $R^2$, $R^3$, $R^4$, $R^5$, and $R^6$ are the same or different, and represent a hydrogen atom, a halogen atom, an alkyl group having 1 to 20 carbon atoms, an aryl group having 6 to 20 carbon atoms, an aralkyl group having 7 to 20 carbon atoms, a silyl group substituted with a hydrocarbon group having 1 to 20 carbon atoms, an alkoxy group having 1 to 20 carbon atoms, an aryloxy group having 6 to 20 carbon atoms, an aralkyloxy group having 7 to 20 carbon atoms, or an amino group substituted with a hydrocarbon group having 1 to 20 carbon atoms,
$R^7$ represents an alkyl group having 1 to 20 carbon atoms, an aryl group having 6 to 20 carbon atoms, or an aralkyl group having 7 to 20 carbon atoms,
provided that, in $R^1$ to $R^7$, the alkyl group, the aryl group, the aralkyl group, the alkoxy group, the aryloxy group, the aralkyloxy group or the hydrocarbon group may be substituted with a halogen atom,
$R^1$ and $R^2$ may be bonded together to form a ring,
the adjacent groups of $R^3$, $R^4$, $R^5$ and $R^6$ may optionally be bonded together to form a ring, respectively, m Xs are the same or different, and represent a monoanionic ligand, n Ys are the same or different, and represent a neutral ligand, m represents an integer of 1 to 3, and n represents an integer of 0 to 3.

According to the second aspect, the present invention provides a process for producing a rare earth metal complex represented by the formula (1) comprising the step of reacting a substituted or unsubstituted cyclopentadiene compound represented by the formula (2):

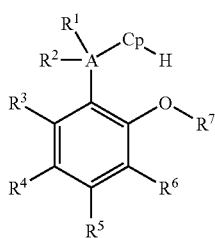

(2)

wherein A, Cp, $R^1$, $R^2$, $R^3$, $R^4$, $R^5$, $R^6$ and $R^7$ are the same as defined above with a rare earth metal compound represented by the formula (3):

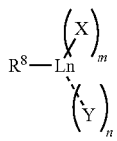

wherein Ln, X, Y, m and n are the same as defined above, and $R^8$ represents an alkyl group optionally substituted with a silyl group substituted with a hydrocarbon group having 1 to 20 carbon atoms, or an aralkyl group optionally substituted with an amino group substituted with a hydrocarbon group having 1 to 20 carbon atoms.

According to the third aspect, the present invention provides a catalytic component for olefin polymerization containing the rare earth metal complex represented by the formula (1).

According to the fourth aspect, the present invention provides a catalyst for olefin polymerization, obtained by contacting the catalytic component for olefin polymerization with at least one compound selected from the group consisting of the following aluminum compounds (A1) to (A3) and the following boron compounds (B1) to (B3):

Aluminum compounds (A):

(A1): an organoaluminum compound represented by the formula:

$(E^1)_aAlZ_{(3-a)}$;

(A2): a cyclic aluminoxane having a structure represented by the formula:

$\{-Al(E^2)-O-\}_b$; and (A3): a linear aluminoxane having a structure represented by the formula:

$E^3\{-Al(E^3)-O-\}_cAl(E^3)_2$ wherein a represents a number satisfying 0<a≦3, b represents an integer of at least 2, c represents an integer of at least 1, $E^1$, $E^2$ and $E^3$ each represent a hydrocarbon group having 1 to 20 carbon atoms, plural $E^1$s, plural $E^2$s and plural $E^3$s may be the same or different, Z represents a hydrogen atom or a halogen atom, and plural Zs may be the same or different; and Boron compounds (B):

(B1): a boron compound represented by the formula:

$BQ^1Q^2Q^3$;

(B2): a boron compound represented by the formula:

$G^+(BQ^1Q^2Q^3Q^4)^-$; and (B3): a boron compound represented by the formula:

$(L^1-H)^+(BQ^1Q^2Q^3Q^4)^-$ wherein B represents a boron atom in the trivalent state, $Q^1$, $Q^2$, $Q^3$ and $Q^4$ each represent independently a halogen atom, a hydrocarbon group, a halogenated hydrocarbon group, a substituted silyl group, an alkoxy group or a disubstituted amino group, $G^+$ represents an inorganic or organic cation, and $L^1$ represents a neutral Lewis base.

According to the fifth aspect, the present invention provides a process for producing an olefin polymer comprising the step of polymerizing an olefin in the presence of the catalyst for olefin polymerization.

According to the sixth aspect, the present invention provides a process for producing a polymer of a polar monomer comprising the step of contacting a polar monomer with the rare earth metal complex represented by the formula (1) to polymerize the monomer.

According to the seventh aspect, the present invention provides a process for producing a polymer of lactones comprising the step of contacting a lactone with the rare earth metal complex represented by the formula (1) to ring-opening polymerizing the lactones.

According to the eighth aspect, the present invention provides a process for producing a polymer of an alkylene oxide comprising the step of contacting an alkylene oxide with the rare earth metal complex represented by the formula (1) to ring-opening polymerize the alkylene oxides.

According to the ninth aspect, the present invention provides a process for producing an acrylate ester polymer or a methacrylate ester polymer comprising the step of contacting an acrylate ester or a methacrylate ester with the rare earth metal complex represented by the formula (1) to polymerize the ester.

EFFECTS OF THE INVENTION

The novel rare earth metal complex of the present invention is useful, for example, as a catalyst for the polymerization reaction of an olefin. In addition, the use of the rare earth metal complex of the present invention as a catalyst makes it possible to polymerize a polar monomer and enables the production of, for example, a lactone polymer having a high molecular weight at a good yield at a relatively low temperature in a short time.

BEST EMBODIMENTS FOR CARRYING OUT THE INVENTION

Examples of the group having a cyclopentadienyl anion moiety represented by Cp in the rare earth metal complex of the formula (1) (hereinafter, abbreviated as a rare earth metal complex (1)) include a cyclopentadienyl group, an indenyl group, and a fluorenyl group, each of which may be substituted or unsubstituted.

Specific examples of the group having a cyclopentadienyl anion moiety include substituted or unsubstituted cyclopentadienyl groups such as a cyclopentadienyl group, a methylcyclopentadienyl group, a dimethylcyclopentadienyl group, a trimethylcyclopentadienyl group, a tetramethylcyclopentadienyl group, an ethylcyclopentadienyl group, a n-propylcyclopentadienyl group, an isopropylcyclopentadienyl group, a n-butylcyclopentadienyl group, a sec-butylcyclopentadienyl group, a tert-butylcyclopentadienyl group, a tetrahydroindenyl group, an octahydrofluorenyl group, a phenylcyclopentadienyl group, a trimethylsilylcyclopentadienyl group, and a tert-butyldimethylsilylcyclopentadienyl group; substituted or unsubstituted indenyl groups such as an indenyl group, a methylindenyl group, a dimethylindenyl group, an ethylindenyl group, a n-propylindenyl group, an isopropylindenyl group, a n-butylindenyl group, a sec-butylindenyl group, a tert-butylindenyl group, and a phenylindenyl group; and a fluorenyl group, and substituted fluorenyl groups such as a 2-methylfluorenyl group, a 2,7-dimethylfluorenyl group, a 2-ethylfluorenyl group, a 2,7-diethylfluorenyl group, a 2-n-propylfluorenyl group, a 2,7-di-n-propylfluorenyl group, a 2-isopropylfluorenyl group, a 2,7-diisopropylfluorenyl group, a 2-n-butylfluorenyl group, a 2-sec-butylfluorenyl group, a 2-tert-butylfluorenyl group, a 2,7-di-n-butylfluorenyl group, a 2,7-di-sec-butylfluorenyl group, a 2,7-di-tert-butylfluorenyl group, a 3,6-di-tert-butylfluorenyl group, a 2-phenylfluorenyl group, a 2,7-di-phenylfluorenyl group, and a 2-methylphenylfluorenyl group, and preferably a cyclopentadienyl group, a methylcyclopentadienyl group, a dimethylcyclopentadienyl group, a trimethylcyclopentadienyl group, a tetramethylcyclopentadienyl group, and a tert-butylcyclopentadienyl group.

In the rare earth metal complex (1) and the substituted or unsubstituted cyclopentadiene compound represented by the formula (2) (hereinafter, abbreviated as a cyclopentadiene compound (2)), examples of the Group 14 element of the periodic table represented by A include a carbon atom, a silicon atom, and a germanium atom, and preferably a carbon atom and a silicon atom.

In substituents $R^1$, $R^2$, $R^3$, $R^4$, $R^5$ and $R^6$, examples of the halogen atom include a fluorine atom, a chlorine atom, a bromine atom, and an iodine atom, and preferably a chlorine atom.

In substituents $R^1$, $R^2$, $R^3$, $R^4$, $R^5$, $R^6$ and $R^7$, specific examples of the alkyl group having 1 to 20 carbon atoms include a methyl group, an ethyl group, a n-propyl group, an isopropyl group, a n-butyl group, a sec-butyl group, a tert-butyl group, a n-pentyl group, a neopentyl group, an amyl group, a n-hexyl group, a heptyl group, a n-octyl group, a n-nonyl group, a n-decyl group, a n-dodecyl group, a n-tridecyl group, a tetradecyl group, a pentadecyl group, a hexadecyl group, a heptadecyl group, an octadecyl group, a nonadecyl group, and a n-eicosyl group, and preferably a methyl group, an ethyl group, an isopropyl group, a tert-butyl group, an amyl group, and the like.

In substituents $R^1$, $R^2$, $R^3$, $R^4$, $R^5$, $R^6$ and $R^7$, specific examples of the halogen-substituted alkyl group having 1 to 20 carbon atoms include the above alkyl groups which are substituted with a halogen atom such as a fluorine atom, a chlorine atom, a bromine atom or an iodine atom.

In substituents $R^1$, $R^2$, $R^3$, $R^4$, $R^5$, $R^6$ and $R^7$, specific examples of the aryl group having 6 to 20 carbon atoms include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenol group, a n-dodecylphenyl group, a n-tetradecylphenyl group, a naphthyl group, and an anthracenyl group, and preferably a phenyl group.

In substituents $R^1$, $R^2$, $R^3$, $R^4$, $R^5$, $R^6$ and $R^7$, specific examples of the aryl group having 6 to 20 carbon atoms substituted with a halogen include the above aryl groups which are substituted with a halogen atom such as a fluorine atom, a chlorine atom, a bromine atom or an iodine atom.

In substituents $R^1$, $R^2$, $R^3$, $R^4$, $R^5$, $R^6$ and $R^7$, specific examples of the aralkyl group having 7 to 20 carbon atoms include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-decylphenyl)methyl group, a naphthylmethyl group, and an anthracenylmethyl group, and preferably a benzyl group.

In substituents $R^1$, $R^2$, $R^3$, $R^4$, $R^5$, $R^6$ and $R^7$, specific examples of the aralkyl group having 7 to 20 carbon atoms substituted with a halogen include the above aralkyl groups which are substituted with a halogen atom such as a fluorine atom, a chlorine atom, a bromine atom or an iodine atom.

In substituents $R^1$, $R^2$, $R^3$, $R^4$, $R^5$, and $R^6$, examples of the hydrocarbon group of the silyl group substituted with the hydrocarbon group include alkyl groups each having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group, a n-heptyl group, a n-octyl group, a n-nonyl group, and a n-decyl group, and aryl groups such as a phenyl group. Specific examples of such a silyl group substituted with hydrocarbon having 1 to 20 carbon atoms include monosubstituted silyl groups having 1 to 20 carbon atoms such as a methylsilyl group, an ethylsilyl group, and a phenylsilyl group, disubstituted silyl groups substituted with hydrocarbon groups each having 1 to 20 carbon atoms such as a dimethylsilyl group, a diethylsilyl group, and a diphenylsilyl group, and trisubstituted silyl groups substituted with a hydrocarbon group having 1 to 20 carbon atoms such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a tri-isobutylsilyl group, a tert-butyl-dimethylsilyl group, a tri-n-pentylsilyl group, a tri-n-hexylsilyl group, a tricyclohexylsilyl group, and a triphenylsilyl group, and preferably a trimethylsilyl group, a tert-butyldimethylsilyl group, and a triphenylsilyl group.

Besides the above-described hydrocarbon groups, examples of the hydrocarbon group constituting a substituted silyl group include hydrocarbon groups substituted with a halogen atom such as a fluorine atom, a chlorine atom, a bromine atom, or an iodine atom.

In substituents $R^1$, $R^2$, $R^3$, $R^4$, $R^5$, and $R^6$, specific examples of the alkoxy group having 1 to 20 carbon atoms include a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, a n-decyloxy group, a n-dodecyloxy group, a n-undecyloxy group, a n-dodecyloxy group, a tridecyloxy group, a tetradecyloxy group, a n-pentadecyloxy group, a hexadecyloxy group, a heptadecyloxy group, an octadecyloxy group, a nonadecyloxy group, and a n-eicosyloxy group, and preferably a methoxy group, an ethoxy group, and a tert-butoxy group.

Specific examples of the alkoxy group having 1 to 20 carbon atoms substituted with a halogen include the above alkoxy groups which are substituted with a halogen atom such as a fluorine atom, a chlorine atom, a bromine atom or an iodine atom.

In substituents $R^1$, $R^2$, $R^3$, $R^4$, $R^5$, and $R^6$, specific examples of the aryloxy group having 6 to 20 carbon atoms include aryloxy groups having 6 to 20 carbon atoms such as a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, and an anthracenoxy group. Specific examples of the aryloxy group having 6 to 20 carbon atoms substituted with a halogen include the above aryloxy groups having 6 to 20 carbon atoms which are substituted with a halogen atom such as a fluorine atom, a chlorine atom, a bromine atom or an iodine atom.

In substituents $R^1$, $R^2$, $R^3$, $R^4$, $R^5$, and $R^6$, specific examples of the aralkyloxy group having 7 to 20 carbon atoms include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl) methoxy group, a (2,6-dimethylphenyl)methoxy group, a (3,4-dimethylphenyl)methoxy group, a (3,5-dimethylphenyl) methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl) methoxy group, a (n-decylphenyl)methoxy group, a naphthylmethoxy group, and an anthracenylmethoxy group, and preferably a benzyloxy group.

Specific examples of the aralkyloxy group having 7 to 20 carbon atoms substituted with a halogen include the above aralkyloxy groups which are substituted with a halogen atom such as a fluorine atom, a chlorine atom, a bromine atom or an iodine atom.

In substituents $R^1$, $R^2$, $R^3$, $R^4$, $R^5$, and $R^6$, the amino group substituted with a hydrocarbon group having 1 to 20 carbon atoms is an amino group substituted with two hydrocarbon groups, and examples of the hydrocarbon group include alkyl groups having 1 to 20 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, and a cyclohexyl group, and aryl groups such as a phenyl group, and these substituents may be bonded together to form a ring. Examples of such an amino group substituted with a hydrocarbon group having 1 to 20 carbon atoms include a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a di-n-decylamino group, a diphenylamino group, a bistrimethylsilylamino group, a bis-tert-butyldimethylsilylamino group, a pyrrolyl group, pyrrolidinyl group, a piperidinyl group, a carbazolyl group, a dihydroindolyl group, and a dihydroisoindolyl group, and preferably a dimethylamino group, a diethylamino group, a pyrrolidinyl group, a piperidinyl group and the like.

Besides the above-described hydrocarbon groups, examples of the hydrocarbon group constituting these substituted amino groups include hydrocarbon groups substituted with a halogen atom such as a fluorine atom, a chlorine atom, a bromine atom, or an iodine atom.

$R^1$ and $R^2$ may be bonded together to form a ring, and adjacent two substituents among $R^3$, $R^4$, $R^5$ and $R^6$ may optionally be bonded together to form a ring.

Examples of the ring formed by bonding $R^1$ and $R^2$, and the ring formed by bonding adjacent two substituents among $R^3$, $R^4$, $R^5$ and $R^6$ include saturated or unsaturated hydrocarbon rings substituted with a hydrocarbon group having 1 to 20 carbon atoms. Specific examples thereof include a cyclopropane ring, a cyclobutane ring, a cyclopentane ring, a cyclohexane ring, a cycloheptane ring, a cyclooctane ring, a benzene ring, a naphthalene ring, and an anthracene ring.

Examples of the rare earth metal complex (1) of the present invention include the following complexes:

[1-(dimethyl{2-methoxy-3-tert-butyl-5-methylphenyl}silyl)-2,3,4,5-tetramethylcyclopentadienyl]bis(o-N,N-dimethylaminobenzyl)scandium,

[1-(diethyl{2-methoxy-3-tert-butyl-5-methylphenyl}silyl)-2,3,4,5-tetramethylcyclopentadienyl]bis(o-N,N-dimethylaminobenzyl)scandium,

[1-(dimethyl{2-methoxy-3-tert-butyl-5-methylphenyl}silyl)-cyclopentadienyl]bis(o-N,N-dimethylaminobenzyl)scandium,

[1-(diethyl{2-methoxy-3-tert-butyl-5-methylphenyl}silyl)-cyclopentadienyl]-bis(o-N,N-dimethylaminobenzyl)scandium,

[1-(dimethyl{2-methoxy-3-tert-butyl-5-methylphenyl}silyl)-2,4-dimethyl-cyclopentadienyl]bis(o—N,N-dimethylaminobenzyl)scandium,
[1-(diethyl{2-methoxy-3-tert-butyl-5-methylphenyl}silyl)-2,4-dimethyl-cyclopentadienyl]bis(o-N,N-dimethylaminobenzyl)scandium,
[1-(dimethyl{2-methoxy-3-tert-butyl-5-methylphenyl}silyl)-2,3,5-trimethyl-cyclopentadienyl]bis(o-N,N-dimethylaminobenzyl)scandium,
[1-(diethyl{2-methoxy-3-tert-butyl-5-methylphenyl}silyl)-2,3,5-trimethyl-cyclopentadienyl]bis(o-N,N-dimethylaminobenzyl)scandium,
[1-(dimethyl{2-methoxy-3-tert-butyl-5-methylphenyl}silyl)-2,3,4,5-tetramethylcyclopentadienyl]bis(trimethylsilylmethyl)scandium,
[1-(diethyl{2-methoxy-3-tert-butyl-5-methylphenyl}silyl)-2,3,4,5-tetramethylcyclopentadienyl]bis(trimethylsilylmethyl)scandium,
[1-(dimethyl{2-methoxy-3-tert-butyl-5-methylphenyl}silyl)cyclopentadienyl]-bis(trimethylsilylmethyl)scandium,
[1-(diethyl{2-methoxy-3-tert-butyl-5-methylphenyl}silyl)cyclopentadienyl]-bis(trimethylsilylmethyl)scandium,
[1-(dimethyl{2-methoxy-3-tert-butyl-5-methylphenyl}silyl)-2,4-dimethyl-cyclopentadienyl]bis(trimethylsilylmethyl)scandium,
[1-(diethyl{2-methoxy-3-tert-butyl-5-methylphenyl}silyl)-2,4-dimethyl-cyclopentadienyl]bis(trimethylsilylmethyl)scandium,
[1-(dimethyl{2-methoxy-3-tert-butyl-5-methylphenyl}silyl)-2,3,5-trimethyl-cyclopentadienyl]bis(trimethylsilylmethyl)scandium,
[1-(diethyl{2-methoxy-3-tert-butyl-5-methylphenyl}silyl)-2,3,5-trimethyl-cyclopentadienyl]bis(trimethylsilylmethyl)scandium,
[1-(dimethyl{2-methoxy-3-tert-butyl-5-methylphenyl}silyl)-2,3,4,5-tetramethylcyclopentadienyl]bis(o-N,N-dimethylaminobenzyl)lutetium,
[1-(diethyl{2-methoxy-3-tert-butyl-5-methylphenyl}silyl)-2,3,4,5-tetramethylcyclopentadienyl]bis(o-N,N-dimethylaminobenzyl)lutetium,
[1-(dimethyl{2-methoxy-3-tert-butyl-5-methylphenyl}silyl)cyclopentadienyl]-bis(o-N,N-dimethylaminobenzyl)lutetium,
[1-(diethyl{2-methoxy-3-tert-butyl-5-methylphenyl}silyl)cyclopentadienyl]-bis(o-N,N-dimethylaminobenzyl)lutetium,
[1-(dimethyl{2-methoxy-3-tert-butyl-5-methylphenyl}silyl)-2,4-dimethyl-cyclopentadienyl]bis(o—N,N-dimethylaminobenzyl)lutetium,
[1-(diethyl{2-methoxy-3-tert-butyl-5 methylphenyl}silyl)-2,4-dimethyl-cyclopentadienyl]bis(o-N,N-dimethylaminobenzyl)lutetium,
[1-(dimethyl){2-methoxy-3-tert-butyl-5-methylphenyl}silyl)-2,3,5-trimethyl-cyclopentadienyl]bis(o-N,N-dimethylaminobenzyl)lutetium,
[1-(diethyl{2-methoxy-3-tert-butyl-5-methylphenyl}silyl)-2,3,5-trimethyl-cyclopentadienyl]bis(o-N,N-dimethylaminobenzyl)lutetium,
[1-(dimethyl{2-methoxy-3-tert-butyl-5-methylphenyl}silyl)-2,3,4,5-tetramethylcyclopentadienyl]bis(trimethylsilylmethyl)lutetium,
[1-(diethyl{2-methoxy-3-tert-butyl-5-methylphenyl}silyl)-2,3,4,5-tetramethylcyclopentadienyl]bis(trimethylsilylmethyl)lutetium,
[1-(dimethyl{2-methoxy-3-tert-butyl-5-methylphenyl}silyl)cyclopentadienyl]-bis(trimethylsilylmethyl)lutetium,
[1-(diethyl{2-methoxy-3-tert-butyl-5-methylphenyl}silyl)cyclopentadienyl]-bis(trimethylsilylmethyl)lutetium,
[1-(dimethyl{2-methoxy-3-tert-butyl-5-methylphenyl}silyl)-2,4-dimethyl-cyclopentadienyl]bis(trimethylsilylmethyl)lutetium,
[1-(diethyl{2-methoxy-3-tert-butyl-5-methylphenyl}silyl)-2,4-dimethyl-cyclopentadienyl]bis(trimethylsilylmethyl)lutetium,
[1-(dimethyl{2-methoxy-3-tert-butyl-5-methylphenyl}silyl)-2,3,5-trimethyl-cyclopentadienyl]bis(trimethylsilylmethyl)lutetium,
[1-(diethyl{2-methoxy-3-tert-butyl-5-methylphenyl}silyl)-2,3,5-trimethyl-cyclopentadienyl]bis(trimethylsilylmethyl)lutetium,
[1-{1'-(2-methoxy-3-tert-butyl-5-methylphenyl)-1-methylethyl}-cyclopentadienyl]bis(o-N,N-dimethylaminobenzyl)yttrium,
[1-{1-(2-methoxy-3-tert-butyl-5-methylphenyl)-1-ethylpropyl}-cyclopentadienyl]bis(o-N,N-dimethylaminobenzyl)yttrium,
[1-{1-(2-methoxy-3-tert-butyl-5-methylphenyl)-1-methylethyl}-3-methyl-cyclopentadienyl]bis(o-N,N-dimethylaminobenzyl)yttrium,
[1-{1-(2-methoxy-3-tert-butyl-5-methylphenyl)-1-ethylpropyl}-3-methyl-cyclopentadienyl]bis(o-N,N-dimethylaminobenzyl)yttrium,
[1-{1-(2-methoxy-3-tert-butyl-5-methylphenyl)-1-methylethyl}-3-tert-butyl-cyclopentadienyl]bis(o-N,N-dimethylaminobenzyl)yttrium,
[1-{1-(2-methoxy-3-tert-butyl-5-methylphenyl)-1-ethylpropyl}-3-tert-butyl-cyclopentadienyl]bis(o-N,N-dimethylaminobenzyl)yttrium,
[1-{1-(2-methoxy-3-tert-butyl-5-methylphenyl)-1-methylethyl}-cyclopentadienyl]bis(trimethylsilylmethyl)yttrium,
[1-{1-(2-methoxy-3-tert-butyl-5-methylphenyl)-1-ethylpropyl}-cyclopentadienyl]bis(trimethylsilylmethyl)yttrium,
[1-{1-(2-methoxy-3-tert-butyl-5-methylphenyl)-1-methylethyl}-3-methyl-cyclopentadienyl]bis(trimethylsilylmethyl)yttrium,
[1-{1-(2-methoxy-3-tert-butyl-5-methylphenyl)-1-ethylpropyl}-3-methyl-cyclopentadienyl]bis(trimethylsilylmethyl)yttrium,
[1-{1-(2-methoxy-3-tert-butyl-5-methylphenyl)-1-methylethyl}-3-tert-butyl-cyclopentadienyl]bis(trimethylsilylmethyl)yttrium,
[1-{1-(2-methoxy-3-tert-butyl-5-methylphenyl)-1-ethypropyl}-3-tert-butyl-cyclopentadienyl]bis(trimethylsilylmethyl)yttrium;

as well as the above compounds in which scandium, lutetium or yttrium is replaced by lanthanum, cerium, praseodymium, neodymium, promethium, samarium, europium, gadolinium, terbium, dysprosium, holmium, erbium, thulium or ytterbium.

The rare earth metal complex (1) can be produced by reacting the cyclopentadiene compound (2) and the rare earth metal compound represented by the formula (3) (hereinafter, abbreviated as a rare earth metal compound (3)).

Examples of the hydrocarbon group having 1 to 20 carbon atoms in the alkyl group optionally substituted with a silyl group substituted with a hydrocarbon group having 1 to 20 carbon atoms in the substituent $R^8$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a heptyl group, a n-octyl group, a n-nonyl group, a n-decyl group, a n-dodecyl group, a n-tridecyl group, a tetradecyl group, a pentadecyl group, a hexadecyl group, a heptadecyl group, an octadecyl group, a nonadecyl group, and a n-eicosyl group, and preferably a methyl group, an ethyl group, an isopropyl group, a tert-butyl group, an amyl group and the like.

Examples of the alkyl group optionally substituted with a silyl group substituted with a hydrocarbon group having 1 to 20 carbon atoms in the substituent $R^8$ include a trimethylsilylmethyl group, a trimethylsilylmethyl group, a triisopropylsilylmethyl group, a tri-n-butylsilylmethyl group, and a tert-butyldimethylsilylmethyl group, and preferably a trimethylsilylmethyl group.

Examples of the hydrocarbon group having 1 to 20 carbon atoms in the aralkyl group substituted with an amino group substituted with a hydrocarbon group having 1 to 20 carbon atoms in the substituent $R^8$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a heptyl group, a n-octyl group, a n-nonyl group, a n-decyl group, a n-dodecyl group, a n-tridecyl group, a tetradecyl group, a pentadecyl group, a hexadecyl group, a heptadecyl group, an octadecyl group, a nonadecyl group, and a n-eicosyl group, and preferably a methyl group, an ethyl group, an isopropyl group, a tert-butyl group, an amyl group and the like.

Examples of the aralkyl group substituted with an amino group substituted with a hydrocarbon group having 1 to 20 carbon atoms in the substituent $R^8$ include an o-N,N-dimethylaminobenzyl group, and an o-N,N-dimethylaminobenzyl group, and preferably an o-N,N-dimethylamino-benzyl group.

The cyclopentadiene compound (2) may be produced by, for example, a known method (see JP-A-09-87313).

Examples of such a cyclopentadiene compound (2) include the following compounds:
(2-methoxyphenyl)(cyclopentadienyl)diethylsilane,
(2-methoxy-3-methylphenyl)(cyclopentadienyl)diethylsilane,
(2-methoxy-3,5-dimethylphenyl)(cyclopentadienyl)diethylsilane,
(2-methoxy-3-tert-butylphenyl)(cyclopentadienyl)diethylsilane,
(2-methoxy-3-tert-butyl-5-methylphenyl)(cyclopentadienyl)diethylsilane,
(2-methoxy-3,5-di-tert-butylphenyl)(cyclopentadienyl)diethylsilane,
(2-methoxy-5-methyl-3-phenylphenyl)(cyclopentadienyl)diethylsilane,
(2-methoxy-5-methyl-3-triethylsilylphenyl)(cyclopentadienyl)diethylsilane,
(2-methoxy-3-tert-butyldimethylsilyl-5-methylphenyl)(cyclopentadienyl)-diethylsilane,
(2-methoxy-3,5-diamylphenyl)(cyclopentadienyl)diethylsilane,
(2-methoxy-3-tert-butyl-5-methoxyphenyl)(cyclopentadienyl)diethylsilane,
(2-methoxy-5-tert-butyl-3-chlorophenyl)(cyclopentadienyl)diethylsilane,
(1-methoxynaphthalen-2-yl)(cyclopentadienyl)diethylsilane,
(2-methoxy-3-tert-butyl-5-methoxyphenyl)(cyclopentadienyl)diethylsilane,
(2-methoxyphenyl(2,3,4,5-tetramethylcyclopentadienyl)diethylsilane,
(2-methoxy-3-methylphenyl)(2,3,4,5-tetramethylcyclopentadienyl)diethylsilane,
(2-methoxy-3,5-dimethylphenyl)(2,3,4,5-tetramethylcyclopentadienyl)-diethylsilane,
(2-methoxy-3-tert-butylphenyl)(2,3,4,5-tetramethylcyclopentadienyl)diethylsilane,
(2-methoxy-3-tert-butyl-5-methylphenyl)(2,3,4,5-tetramethylcyclopentadienyl)diethylsilane,
(2-methoxy-3,5-di-tert-butylphenyl)(2,3,4,5-tetramethylcyclopentadienyl)-diethylsilane,
(2-methoxy-5-methyl-3-phenylphenyl)(2,3,4,5-tetramethylcyclopentadienyl)-diethylsilane,
(2-methoxy-5-methyl-3-triethylsilylphenyl)(2,3,4,5-tetramethylcyclopentadienyl)diethylsilane,
(2-methoxy-3-tert-butyldimethylmethylsilyl-5-methylphenyl)(2,3,4,5-tetramethylcyclopentadienyl)diethylsilane,
(2-methoxy-3,5-diamylphenyl)(2,3,4,5-tetramethylcyclopentadienyl)diethylsilane,
(2-methoxy-3-tert-butyl-5-methoxyphenyl)(2,3,4,5-tetramethylcyclopentadienyl)diethylsilane,
(2-methoxy-5-tert-butyl-3-chlorophenyl)(2,3,4,5-tetramethylcyclopentadienyl)diethylsilane,
(1-methoxynaphthalen-2-yl)(2,3,4,5-tetramethylcyclopentadienyl)diethylsilane,
(2-methoxy-3-tert-butyl-5-methoxyphenyl)(2,3,4,5-tetramethylcyclopentadienyl)diethylsilane, and the like;

as well as the above in which diethylsilane is replaced by dimethylsilane, diphenylsilane, ethylmethylsilane, methylphenylsilane, dimethylmethane, or dimethylmethane,
2-[1-(cyclopentadienyl)-1-methylethyl]-1-methoxybenzene,
2-[1-(cyclopentadienyl)-1-methylethyl]-1-methoxy-4,6-dimethylbenzene,
6-tert-butyl-2-[1-(cyclopentadienyl)-1-methylethyl]-1-methoxy-4-methylbenzene,
6-[1-(cyclopentadienyl)-1-methylethyl]-1-methoxy-2-phenylbenzene,
1-tert-butyldimethylsilyl-3-[1-(cyclopentadienyl)-1-methylethyl]-2-methoxy-5-methylbenzene,
3-[1-(cyclopentadienyl)-1-methylethyl]-2-methoxy-5-methyl-1-trimethylsilylbenzene,
6-tert-butyl-2-[1-(cyclopentadienyl)-1-methylethyl]-1,4-dimethoxybenzene,
5-tert-butyl-1-chloro-3-[1-(cyclopentadienyl)-1-methylethyl]-4-methoxybenzene,
6-tert-butyl-2-[1-(cyclopentadienyl)-1-methylethyl]-1-methoxybenzene,
1-methoxy-2-[1-(4-methyl-cyclopentadienyl)-1-methylethyl]benzene,
1-methoxy-4,6-dimethyl-2-[1-(4-methyl-cyclopentadienyl)-1-methylethyl]-benzene,
6-tert-butyl-1-methoxy-4-methyl-2-[1-(4-methyl-cyclopentadienyl)-1-methyl-ethyl]benzene,
1-methoxy-6-[1-(4-methyl-cyclopentadienyl)-1-methylethyl]-2-phenylbenzene,
1-tert-butyldimethylsilyl-2-methoxy-5-methyl-3-[1-(4-methyl-cyclopentadienyl)-1-methylethyl]benzene,
2-methoxy-5-methyl-3-[1-(4-methyl-cyclopentadienyl)-1-methylethyl]-1-trimethylsilylbenzene,
6-tert-butyl-1,4-dimethoxy-2-[1-(4-methyl-cyclopentadienyl)-1-methylethyl]-benzene,
5-tert-butyl-1-chloro-4-methoxy-3-[1-(4-methyl-cyclopentadienyl)-1-methyl-ethyl]benzene,
6-tert-butyl-1-methoxy-2-[1-(4-methyl-cyclopentadienyl)-1-methylethyl]-benzene,
2-[1-(4-tert-butyl-cyclopentadienyl)-1-methylethyl]-1-methoxybenzene,
2-[1-(4-tert-butyl-cyclopentadienyl)-1-methylethyl]-1-methoxy-4,6-dimethylbenzene, 6-tert-butyl-2-[1-(4-tert-butyl-cyclopentadienyl)-1-methylethyl]-1-methoxy-4-methylbenzene,
6-[1-(4-tert-butyl-cyclopentadienyl)-1-methylethyl]-1-methoxy-2-phenylbenzene,
1-tert-butyldimethylsilyl-3-[1-(4-tert-butyl-cyclopentadienyl)-1-methylethyl]-2-methoxy-5-methylbenzene,
3-[1-(4-tert-butylcyclopentadienyl)-1-methylethyl]-2-methoxy-5-methyl-1-trimethylsilylbenzene,
6-tert-butyl-2-[1-(4-tert-butyl-cyclopentadienyl)-1-methylethyl]-1,4-dimethoxybenzene,
5-tert-butyl-1-chloro-3-[1-(4-tert-butyl-cyclopentadienyl)-1-methylethyl]-4-methoxybenzene,
6-tert-butyl-2-[1-(4-tert-butyl-cyclopentadienyl)-1-methylethyl]-1-methoxybenzene and the like;

as well as the above compounds in which methoxy is replaced by ethoxy, isopropoxy, phenoxy, or benzyloxy.

Examples of the monoanionic ligand represented by the substituent X in the rare earth metal complex (1) and the rare earth metal compound (3) include a hydrogen atom, a halogen atom, a methyl group, an ethyl group, a n-butyl group, a neopentyl group, a phenyl group, a neopentylidene group, a methoxy group, a tert-butoxy group, a phenoxy group, a benzyl group, an amide group, a phosphino group, a trimethylsilylmethyl group, a bis(trimethylsilyl)methyl group, a bis(trimethylsilyl)amide group, and an o-dimethylaminobenzyl group, and preferably a methyl group, a trimethylsilylmethyl group, and an o-dimethylaminobenzyl group.

When m is 2, two Xs may be bonded together, or may be taken together to form a dianionic ligand.

Examples of the neutral ligand represented by the substituent Y in the rare earth metal complex (1) and the rare earth metal compound (3) include olefins, aromatic compounds, ethers, sulfides, amines, nitriles, phosphines, and phosphine oxides, and preferably ethers and amines.

Specific examples of the neutral ligand represented by Y include ethylene, propylene, 1-butene, cyclooctadiene, styrene, benzene, toluene, naphthalene, anthracene, diethyl ether, tetrahydrofuran, 1,2-dimethoxyethane, dimethyl sulfide, thiophene, tetrahydrothiophene, trimethylamine, triethylamine, ethyldiisopropylamine, N,N-dimethylaniline, N,N,N',N'-tetramethylethylenediamine, pyridine, N,N-dimethylaminopyridine, acetonitrile, trimethylphosphine, triethylphosphine, tri-tert-butylphosphine, tricyclohexylphosphine, triphenylphosphine, trimethylphosphine oxide, and triphenylphosphine oxide, and preferably tetrahydrofuran, diethyl ether, N,N-dimethylaniline, and trimethylphosphine.

X and Y may be bonded together to form a multidentate ligand.

Specific examples of the multidentate ligand include an o-N,N-dimethylaminobenzyl group.

In the formulae (1) and (3), m represents an integer of 1 to 3, preferably 1 or 2, more preferably 2, and n represents an integer of 0 to 3, preferably 0 to 2, more preferably 0 or 2.

Such a rare earth metal compound (3) may be synthesized by a known process (see J. Am. Chem. Soc., 1978, 100, 8068, or J. Chem. Soc., Chem. Comm., 1973, 126).

Examples of such a rare earth metal compound (3) include tris(trimethylsilylmethyl)scandium, tris(o-N,N-dimethylaminobenzyl)scandium and the like, and may be adducts of these compounds with diethyl ether, tetrahydrofuran, trimethylamine, triethylamine, N,N-dimethylaniline and N,N,N',N'-tetramethylethylene-diamine. Additional examples include the above compounds in which scandium is replaced by yttrium, lanthanum, cerium, praseodymium, neodymium, promethium, samarium, europium, gadolinium, terbium, dysprosium, holmium, erbium, thulium, ytterbium or lutetium. More preferable examples include tris(o-N,N-dimethylaminobenzyl)scandium, tris(o—N,N-dimethylaminobenzyl)yttrium, and tris(o-N,N-dimethylaminobenzyl)lutetium.

A reaction between the cyclopentadiene compound (2) and the rare earth metal compound (3) may be usually performed by adding the cyclopentadiene compound (2) to a solvent followed by the addition of the rare earth metal compound (3).

An amount of the rare earth metal compound (3) is usually 0.5 to 3 moles, preferably 0.7 to 1.5 moles per 1 mole of the cyclopentadiene compound (2).

A reaction temperature is usually from −100° C. to the boiling point of a solvent, preferably in a range of −80° C. to 60° C.

The reaction is usually performed in a solvent inert to the reaction. Examples of such a solvent include aromatic hydrocarbons such as benzene and toluene; aliphatic hydrocarbons such as hexane and heptane; ethers such as diethyl ether, tetrahydrofuran, and 1,4-dioxane; amides such as hexamethylphosphoric amide, and dimethylformamide; polar solvents such as acetonitrile, propionitrile, acetone, diethyl ketone, methyl isobutyl ketone, and cyclohexanone; and aprotic solvents such as halogenated solvents such as dichloromethane, dichloroethane, chlorobenzene and dichlorobenzene. Such solvents may be used alone or as a mixture of two or more of them, and an amount thereof is usually 1 to 200 parts by weight, preferably 3 to 50 parts by weight per 1 part by weight of the cyclopentadiene compound (2).

After the completion of the reaction, an desired rare earth metal complex (1) can be obtained from the resultant reaction mixture by a conventional method, for example, by filtering the produced precipitate, concentrating the filtrate to precipitate a rare earth metal complex (1), and collecting the complex by filtration.

[Catalyst for Olefin Polymerization]

The catalyst for olefin polymerization of the present invention is a catalyst for olefin polymerization comprising the rare earth metal complex (1) as a component of the catalyst for olefin polymerization, and is obtained by contacting the rare earth metal complex (1) with other co-catalytic component. Examples of the catalyst for olefin polymerization include catalysts for olefin polymerization obtained by contacting the rare earth metal complex (1) with at least one compound selected from the group consisting of the following aluminum compounds (A1) to (A3) and the following boron compounds (B1) to (B3);

Aluminum compounds (A):

(A1): an organoaluminum compound represented by the formula:

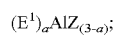

(A2): a cyclic aluminoxane having a structure represented by the formula:

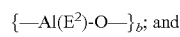

(A3): a linear aluminoxane having a structure represented by the formula:

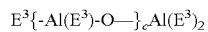

wherein a represents a number satisfying $0 < a \leq 3$, b represents an integer of at least 2, c represents an integer of at least 1, $E^1$, $E^2$ and $E^3$ each represent a hydrocarbon group having 1 to 20 carbon atoms, plural $E^1$s, plural $E^2$s and plural $E^3$s may be the same or different, Z represents a hydrogen atom or a halogen atom, and plural Zs may be the same or different); and Boron compounds (B):

(B1): a boron compound represented by the formula:

$BQ^1Q^2Q^3$;

(B2): a boron compound represented by the formula:

$G^+(BQ^1Q^2Q^3Q^4)^-$; and (B3): a boron compound represented by the formula:

$(L^1\text{-}H)^+(BQ^1Q^2Q^3Q^4)^-$ wherein B represents a boron atom in the trivalent state, $Q^1$, $Q^2$, $Q^3$ and $Q^4$ each represent independently a halogen atom, a hydrocarbon group, a halogenated hydrocarbon group, a substituted silyl group, an alkoxy group or a di-substituted amino group, $G^+$ represents an inorganic or organic cation, and $L^1$ represents a neutral Lewis base.

Examples of the organoaluminum compound (A1) represented by the formula: $(E^1)_a AlZ_{(3-a)}$ include trialkylaluminums such as trimethylaluminum, triethylaluminum, tripropylaluminum, triisobutylaluminum, and trihexylaluminum; dialkylaluminum chlorides such as dimethylaluminum chloride, diethylaluminum chloride, dipropylaluminum chloride, diisobutylaluminum chloride, and dihexylaluminum chloride; alkylaluminum dichlorides such as methylaluminum dichloride, ethylaluminum dichloride, propylaluminum dichloride, isobutylaluminum dichloride, and hexylaluminum dichloride; dialkylaluminum hydrides such as dimethylaluminum hydride, diethylaluminum hydride, dipropylaluminum hydride, diisobutylaluminum hydride, and dihexylaluminum hydride. Preferable is trialkylaluminum, and more preferable is triethylaluminum or triisobutylaluminum.

Examples of $E^2$ and $E^3$ in the cyclic aluminoxane (A2) having a structure represented by the formula: $\{-Al(E^2)-O-\}_b$ or the linear aluminoxane (A3) having a structure represented by the formula: $E^3\{-Al(E^3)-O-\}_c Al(E^3)_2$ include alkyl groups such as a methyl group, an ethyl group, a n-propyl group, an isopropyl group, a n-butyl group, an isobutyl group, a n-pentyl group, and a neopentyl group. Here, b is an integer of at least 2, and c is an integer of at least 1. Preferably, $E^2$ and $E^3$ are each independently a methyl group or an isobutyl group, b is 2 to 40, and c is 1 to 40.

The aluminoxane is prepared by a variety of processes. The process is not particularly limited, and the aluminoxane may be prepared by a known method. For example, the aluminoxane is prepared by contacting a solution of a trialkylaluminum (e.g. trimethylaluminum) dissolved in an appropriate organic solvent (benzene or an aliphatic hydrocarbon) with water. Additional examples include a method of contacting a trialkylaluminum (e.g. trimethylaluminum) with a metal salt containing crystal water (e.g. copper sulfate hydrate).

In the boron compound (B1) represented by the formula: $BQ^1Q^2Q^3$, B is a boron atom in the trivalent state. $Q^1$ to $Q^3$ each are independently, preferably, a halogen atom, a hydrocarbon group having 1 to 20 carbon atoms, a halogenated hydrocarbon group having 1 to 20 carbon atoms, a substituted silyl group having 1 to 20 carbon atoms, an alkoxy group having 1 to 20 carbon atoms or a disubstituted amino group having 2 to 20 carbon atoms, more preferably a halogen atom, a hydrocarbon group having 1 to 20 carbon atoms, or a halogenated hydrocarbon group having 1 to 20 carbon atoms.

Examples of the boron compound (B1) represented by the formula $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, and preferably tris(pentafluorophenyl)borane.

In the boron compound (B2) represented by the formula: $G^+(BQ^1Q^2Q^3Q^4)^-$, $G^+$ is an inorganic or organic cation, B is a boron atom in the trivalent state, and $Q^1$ to $Q^4$ are the same as defined for $Q^1$ to $Q^3$ in the (B1).

In the boron compound (B2) represented by $G^+(BQ^1Q^2Q^3Q^4)^-$, examples of inorganic cation $G^+$ include a ferrocenium cation, an alkyl-substituted ferrocenium cation, and a silver cation, and examples of organic cation $G^+$ include a triphenylmethyl cation. Examples of $(BQ^1Q^2Q^3Q^4)$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate, and tetrakis(3,5-bistrifluoromethylphenyl)borate.

Examples of the boron compound (B2) represented by the formula: $G^+(BQ^1Q^2Q^3Q^4)^-$ include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, and triphenylmethyl tetrakis(3,5-bistrifluoromethylphenyl)borate, and preferably triphenylmethyl tetrakis(pentafluorophenyl)borate.

In the boron compound (B3) represented by the formula: $(L^1\text{-}H)^+(BQ^1Q^2Q^3Q^4)^-$, $L^1$ is a neutral Lewis base, $(L^1\text{-}H)^+$ is a Brønsted acid, B is a boron atom in the trivalent state, and $Q^1$ to $Q^4$ are the same as defined for $Q^1$ to $Q^3$ in the (B1).

In the boron compound (B3) represented by the formula: $(L^1\text{-}H)^+(BQ^1Q^2Q^3Q^4)^-$, examples of $(L^1\text{-}H)^+$ include trialkyl-substituted ammonium, N,N-dialkylanilinium, dialkylammonium, and triarylphosphonium, and examples of $(BQ^1Q^2Q^3Q^4)^-$ include the same cations as those described above.

Examples of the boron compound (B3) represented by the formula $(L^1\text{-}H)^+(BQ^1Q^2Q^3Q^4)^-$ include triethylammonium tetrakis(pentafluorophenylborate, tripropylammonium tetrakis(pentafluorophenyl)borate, tri(normalbutyl)ammonium tetrakis(pentafluorophenyl)borate, tri(normalbutyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, and tri(dimethylphenyl)phosphonium tetrakis(pentafluorophenyl)borate, and preferably tri(normalbutyl)ammonium tetrakis(pentafluorophenyl)borate and N,N-dimethylanilinium tetrakis(pentafluorophenyl)borate.

As the compound (B), usually, any one of the boron compound (B1) represented by the formula: $BQ^1Q^2Q^3$, the boron compound (B2) represented by the formula: $G^+(BQ^1Q^2Q^3Q^4)^-$ and the boron compound (B3) represented by the formula: $(L^1\text{-}H)^+(BQ^1Q^2Q^3Q^4)^-$ is used.

In the method of contacting catalytic components with each other in production of the catalyst for olefin polymerization, any two catalytic components may be contacted with each other in advance and, thereafter, the remaining catalytic component may be contacted therewith. Alternatively, catalytic components may be contacted with each other in a polymerization reactor, or respective catalytic components may be separately charged into a polymerization reactor in an arbitrary order, or arbitrary two or more catalytic components which have been contacted with each other in advance may be charged therein.

Regarding the amount of the catalytic components, the molar ratio of the compound (A) (in terms of aluminum atom) to the rare earth metal complex (1) is usually 0.1:1 to 10000:1, preferably 5:1 to 2000:1. When the organoaluminum compound (A1) is used as the compound (A), the molar ratio of the compound (A) to the rare earth metal complex (1) is more preferably 0.3:1 to 500:1, further preferably 0.5:1 to 100:1. In addition, the molar ratio of compound (B) to the rare earth metal complex (1) is usually 0.01:1 to 100:1, preferably 0.5:1 to 10:1.

Regarding a concentration when each catalytic component is used in a solution state, the concentration of the rare earth metal complex (1) is usually 0.0001 to 5 mmol/liter, preferably 0.001 to 1 mmol/liter, the concentration of the compound (A) in terms of an aluminum atom is usually 0.01 to 500 mmol/liter, preferably 0.1 to 100 mmol/liter, and the concentration of the compound (B) is usually 0.001 to 5 mmol/liter, preferably 0.001 to 1 mmol/liter.

[Process for Producing Olefin Polymer]

In the process for producing the olefin polymer of the present invention, an olefin is polymerized in the presence of the catalyst for olefin polymerization comprising the rare earth metal complex (1) as a component of the catalyst for olefin polymerization.

As the olefin used in polymerization, a linear olefin, a cyclic olefin and the like may be used, and a single olefin is homopolymerized, or two or more olefins are copolymerized. Usually, an olefin having 2 to 20 carbon atoms is used.

Examples of the linear olefin include ethylene; α-olefins having 3 to 20 carbon atoms such as propylene, 1-butene, 1-pentene, 1-hexene, 1-heptene, 1-octene, 1-nonene, 1-decene, 3-methyl-1-pentene, 4-methyl-1-pentene, 3,3-dimethyl-1-butene, 5-methyl-1-hexene, and 3,3-dimethyl-1-pentene; non-conjugated dienes such as 1,5-hexadiene, 1,4-hexadiene, 1,4-pentadiene, 1,5-heptadiene, 1,6-heptadiene, 1,6-octadiene, 1,7-octadiene, 1,7-nonadiene, 1,8-nonadiene, 1,8-decadiene, 1,9-decadiene, 1,12-tetradecadiene, 1,13-tetradecadiene, 4-methyl-1,4-hexadiene, 5-methyl-1,4-hexadiene, 7-methyl-1,6-octadiene, 3-methyl-1,4-hexadiene, 3-methyl-1,5-hexadiene, 3-ethyl-1,4-hexadiene, 3-ethyl-1,5-hexadiene, 3,3-dimethyl-1,4-hexadiene, and 3,3-dimethyl-1,5-hexadiene; conjugated dienes such as 1,3-butadiene, isoprene, 1,3-hexadiene, and 1,3-octadiene.

Examples of the cyclic olefin as an alicyclic compound include monoolefins such as vinylcyclopentane, vinylcyclohexane, vinylcycloheptane, norbornene, 5-methyl-2-norbornene, 5-ethyl-2-norbornene, 5-butyl-2-norbornene, tetracyclododecene, tricyclodecene, tricycloundecene, pentacyclopentadecene, pentacyclohexadecene, 8-methyltetracyclododecene, and 8-ethyltetracyclododecene; non-conjugated dienes such as 5-ethylidene-2-norbornene, dicyclopentadiene, 5-vinyl-2-norbornene, norbornadiene, 5-methylene-2-norbornene, 1,5-cyclooctadiene, 7-methyl-2,5-norbornadiene, 7-ethyl-2,5-norbornadiene, 7-propyl-2,5-norbornadiene, 7-butyl-2,5-norbornadiene, 7-pentyl-2,5-norbornadiene, 7-hexyl-2,5-norbornadiene, 7,7-dimethyl-2,5-norbornadiene, 7,7-methylethyl-2,5-norbornadiene, 7-chloro-2,5-norbornadiene, 7-bromo-2,5-norbornadiene, 7-fluoro-2,5-norbornadiene, 7,7-dichloro-2,5-norbornadiene, 1-methyl-2,5-norbornadiene, 1-ethyl-2,5-norbornadiene, 1-propyl-2,5-norbornadiene, 1-butyl-2,5-norbornadiene, 1-chloro-2,5-norbornadiene, 1-bromo-2,5-norbornadiene, 5,8-endomethylenehexahydronaphthalene, and vinylcyclohexene; conjugated dienes such as 1,3-cyclooctadiene, and 1,3-cyclohexadiene. In addition, examples of the aromatic compound include styrene, o-methylstyrene, m-methylstyrene, p-methylstyrene, o,p-dimethylstyrene, o-ethylstyrene, m-ethylstyrene, p-ethylstyrene, α-methylstyrene, and divinylbenzene.

Examples of the combination of olefins when olefins are copolymerized include combinations of linear olefin/linear olefin such as ethylene/propylene, ethylene/1-butene, ethylene/1-hexene, ethylene/propylene/1-butene, ethylene/propylene/1-hexene, propylene/1-butene, and propylene/1-hexene; combinations of linear olefin/cyclic olefin such as ethylene/vinylcyclohexane, ethylene/norbornene, ethylene/tetrachlorododecane, ethylene/5-ethylidene-2-norbornene, propylene/vinylcyclohexane, propylene/norbornene, propylene/tetracyclododecene, propylene/5-ethylidene-2-norbornene, and ethylene/propylene/5-ethylidene-2-norbornene.

The polymerization process is not particularly limited, and for example, solution polymerization or slurry polymerization using an aliphatic hydrocarbon (butane, pentane, hexane, heptane, octane or the like), an aromatic hydrocarbon (benzene, toluene or the like) or a halogenated hydrocarbon (methylene dichloride or the like) as a solvent, vapor phase polymerization in a gaseous monomer or the like is possible, and either continuous polymerization or batch polymerization is possible.

A polymerization temperature is usually in a range of −50° C. to 300° C., particularly in a range of −20° C. to 250° C. A polymerization pressure is preferably an atmospheric pressure to 90 MPa. In general, a polymerization time is determined appropriately depending on the kind of the intended polymer, and a reactor, and a time in a range of 1 minute to 20 hours may be adopted. Furthermore, in the present invention, a chain transfer agent such as hydrogen may be added in order to adjust the molecular weight of a polymer.

<Process for Producing Polymer of Polar Monomer>

Using the rare earth complex (1) of the present invention, a polar monomer may be homopolymerized, or a certain polar monomer and a different polar monomer may be copolymerized. The kind of the polar monomer is not particularly limited, and examples thereof include lactones, alkylene oxides, (meth)acrylate esters and the like.

[Process for Producing Lactone Polymer]

Examples of the lactones used in the present invention include β-propiolactone, γ-butyrolactone, δ-valerolactone, ε-caprolactone, β-methylpropiolactone, 3,3,5-trimethyl-ε-caprolactone and the like, and preferably ε-caprolactone.

These lactones may be polymerized alone while a mixture of two or more lactones may be copolymerized. A method of copolymerizing two or more lactones is not particularly limited, and examples thereof include a method of initiating polymerization under such a condition that two or more lactones are present simultaneously to obtain a random copolymer, and a method of polymerizing the first lactone in advance, and then adding the second or subsequent lactone(s) to obtain a block copolymer.

The polymerization method is not particularly limited, and for example, solution polymerization or slurry polymerization using an aliphatic hydrocarbon (butane, pentane, hexane, heptane, octane or the like), an aromatic hydrocarbon (benzene, toluene or the like) or a halogenated hydrocarbon (methylene dichloride or the like) as a solvent can be employed, and either continuous polymerization or batch polymerization is possible.

A polymerization temperature is usually in a range of −80° C. to 150° C., particularly in a range of −30° C. to 100° C. In general, a polymerization time is determined appropriately depending on the kind of the intended polymer, and a reactor and, for example, a time in a range of 1 second to 24 hours can be adopted.

Preferably, the polymerization reaction is performed under an atmosphere of an inert gas such as nitrogen or argon. It is important for the efficient preparation of a polymer that the inert gas and the lactone monomer are sufficiently dried so as to be free from water.

The resultant lactone polymer contains a metal catalytic component. However, when a polymerization degree is high, it is not necessary to remove the metal catalytic component since the content of the contained metal catalytic component is relatively small. When the removal of the metal catalytic component is necessary, the lactone polymer as produced is washed with water or dilute hydrochloric acid to remove the metal catalytic component, followed by drying, to obtain the lactone polymer containing no metal catalytic component.

It is possible to produce a polymer of lactones of the present invention at a relatively low temperature. In this case, the polymer has such characteristics that it has excellent color tone, and little odor, since the amount of mixed impurities generated by depolymerization or thermal degradation of the lactone polymer is small.

The resultant lactone polymer may be pelletized with an extruder, and can be used as a film, a fiber, an expanded sheet or various molded articles.

[Process for Producing Alkylene Oxide Polymer]

Examples of the alkylene oxide used in the present invention include α-olefin oxides having 2 to 9 carbon atoms such as ethylene oxide, propylene oxide, butylene oxide, cyclohexene oxide, cycloheptene oxide, and cyclooctene oxide, α-olefin oxides having 10 or more carbon atoms, styrene oxide, and epichlorohydrin.

These alkylene oxides may be polymerized alone, while a mixture of two or more alkylene oxides may be copolymerized. A method of copolymerizing two or more alkylene oxides is not particularly limited, and examples thereof include a method of initiating polymerization under such a condition that two or more alkylene oxides are present simultaneously to obtain a random copolymer, and a method of polymerizing the first alkylene oxide in advance, and then adding the second or subsequent alkylene oxide(s) to obtain a block copolymer.

A method of initiating polymerization is not particularly limited. For example, an alkylene oxide is added to the solution of the rare earth metal complex (1) to initiate polymerization, or the rare earth metal complex (1) is added to the solution of an alkylene oxide to initiate polymerization.

A polymerization method is not particularly limited, and solution polymerization or slurry polymerization using an aliphatic hydrocarbon (butane, heptane, hexane, heptane, octane or the like), an aromatic hydrocarbon (benzene, toluene or the like), an ether (diethyl ether, tetrahydrofuran, 1,4-dioxane or the like), or a halogenated hydrocarbon (dichloromethane, dichloroethane or the like) can be employed, and either continuous polymerization or batch polymerization is possible.

A polymerization temperature is usually in a range of −80° C. to 150° C., particularly in a range of −30° C. to 100° C. In general, a reaction time is determined appropriately depending on the kind of the intended polymer, and a reactor, and for example, a time in a range of 1 second to 24 hours can be adopted.

Preferably, the polymerization reaction is performed under an atmosphere of an inert gas such as nitrogen or argon. It is important for the efficient preparation of a polymer that the inert gas and an alkylene oxide are sufficiently dried so as to be free from water.

The resultant alkylene oxide polymer contains a metal catalytic component. However, when a polymerization degree is high, it is not necessary to remove the metal catalytic component since the content of the contained metal catalytic component is relatively small. When the removal of the metal catalytic component is necessary, the alkylene oxide polymer as produced is washed with water or dilute hydrochloric acid to remove the metal catalytic component, followed by drying, to obtain an alkylene oxide polymer.

The resultant alkylene oxide polymer can be used as a film, a fiber, an expanded sheet or various molded articles.

[Process for Producing (Meth)Acrylate Ester Polymer]

Examples of the (meth)acrylate ester used in the present invention include methacrylate esters such as methyl methacrylate, ethyl methacrylate, isopropyl methacrylate, n-butyl methacrylate, tert-butyl methacrylate, cyclohexyl methacrylate, isobutyl methacrylate, benzyl methacrylate, allyl methacrylate, and isobornyl methacrylate; and acrylate esters such as methyl acrylate, ethyl acrylate, isopropyl acrylate, n-butyl acrylate, and tert-butyl acrylate.

These (meth)acrylate esters may be polymerized alone, while a mixture of two or more (meth)acrylate esters may be copolymerized. A method of copolymerizing two or more (meth)acrylate esters is not particularly limited, and examples thereof include a method of initiating polymerization under such a condition that two or more (meth)acrylate esters are present simultaneously, to obtain a random copolymer, and a method of polymerizing the first (meth)acrylate ester in advance, and then adding the second or subsequent (meth)acrylate ester(s) to obtain a block copolymer.

A method of initiating polymerization is not particularly limited. For example, a (meth)acrylate ester is added to the solution of the rare earth metal complex (1) to initiate polymerization, or the rare earth metal complex (1) is added to the solution of a (meth)acrylate ester to initiate polymerization.

The polymerization method is not particularly limited, and for example, solution polymerization or slurry polymerization using an aliphatic hydrocarbon (butane, pentane, hexane, heptane, octane or the like), an aromatic hydrocarbon (benzene, toluene or the like), an ether (diethyl ether, tetrahydrofuran, 1,4-dioxane or the like), or a halogenated hydrocarbon (dichloromethane, dichloroethane or the like) as a solvent can be employed, and either continuous polymerization or batch polymerization can be employed.

A polymerization temperature is usually in a range of −80° C. to 150° C., particularly preferably in a range of −30° C. to 100° C. In general, a polymerization time is determined appropriately depending on the kind of the intended polymer, and a reactor and, for example, a time in a range of 1 second to 24 hours can be adopted.

Preferably, the polymerization reaction is performed under an atmosphere of an inert gas such as nitrogen or argon. It is important for the efficient preparation of a polymer that the inert gas and a (meth)acrylate ester monomer are sufficiently dried so as to be free from water.

The resultant (meth)acrylate ester polymer contains a metal catalytic component. However, when a polymerization degree is high, it is not necessary to remove the metal catalytic component since the content of the contained metal catalytic component is relatively small. When the removal of the metal catalytic component is necessary, the (meth)acrylate ester polymer as produced is washed with water or dilute hydrochloric acid to remove the metal catalytic component, followed by drying, to obtain the (meth)acrylate ester polymer.

The resultant (meth)acrylate ester polymer can be used as a film, a fiber, an expanded sheet or various molded articles. Alternatively, the resultant (meth)acrylate ester polymer can be used as an additive for other polymers.

EXAMPLES

The following examples illustrate the present invention in more detail, but they do not limit the present invention in any way.

<Production of Rare Earth Metal Complex>

Physical properties were measured by the following methods.

(1) Proton Nuclear Magnetic Resonance Spectrum ($^1$H-NMR)

Apparatus: EX270 manufactured by JEOL Ltd., or DPX-300 manufactured by Bruker

Sample cell: 5 mmϕ tube

Measurement solvent: $CDCl_3$ or toluene-$d_8$

Sample concentration: 10 mg/0.5 mL ($CDCl_3$ or toluene-$d_8$)

Measurement temperature: room temperature (about 25° C.)

Measurement parameters: 5 mmϕ probe, MENUF NON, OBNUC $^1$H,

Accumulation times 16

Pulse angle: 45 degrees

Repetition time: ACQTM 3 seconds, PD 4 seconds

Internal standard: $CDCl_3$ (7.26 ppm), toluene-$d_8$ (2.09 ppm)

(2) Carbon Nuclear Magnetic Resonance Spectrum ($^{13}$C-NMR)

Apparatus: EX270 manufactured by JEOL Ltd., or DPX-300 manufactured by Bruker

Sample cell: 5 mmϕ tube

Measurement solvent: $CDCl_3$ or toluene-$d_8$

Sample concentration: 30 mg/0.5 mL ($CDCl_3$ or toluene-$d_8$)

Measurement temperature: room temperature (about 25° C.)

Measurement parameter: 5 mmϕ probe, MENUF NON, OBNUC $^{13}$C, accumulation times 256

Pulse angle: 45 degrees

Repetition time: ACQTM 1.8 seconds, PD 1.2 seconds

Internal standard: $CDCl_3$ (77.47, 77.00, 76.53 ppm)

(3) Mass Spectrum

[Electron Ionization Mass Spectroscopy (EI-MS)]

Apparatus: JMS-T100GC manufactured by JEOL Ltd.

Ionization voltage: 70 eV

Ion source temperature: 230° C.

Acceleration voltage: 7 kV

Mass range: m/z 35-1000

Example 1

Synthesis of (2-methoxy-3-tert-butyl-5-methylphenyl)chlorodimethylsilane

Under nitrogen atmosphere, 2-methoxy-1-bromo-3-tert-butyl-5-methylbenzene (20.00 g, 77.77 mmol) was dissolved in 200 mL of diethyl ether. A 1.57 M hexane solution of n-butyllithium (59.44 mL, 93.32 mmol) was dropwise added at −50° C. or lower, and a temperature was raised to room temperature, followed by stirring for 1 hour. All the amount of diethyldichlorosilane (24.44 g, 155.54 mmol) was added to the mixture at once at −50° C. or lower, and a temperature was gradually raised to room temperature. After being refluxed for 1 hour, the solution was concentrated under reduced pressure. Hexane was added, the insolubles were filtered off with a Celite filter, and the filtrate was concentrated under reduced pressure. Concentration was further continued at 70° C. under reduced pressure for 3 hours to obtain (2-methoxy-3-tert-butyl-5-methylphenyl)chlorodimethylsilane. Resultant (2-methoxy-3-tert-butyl-5-methylphenyl)chlorodimethylsilane was used in a subsequent reaction without further purification.

$^1$H-NMR ($CDCl_3$, δ (ppm)): 1.04-1.17 (m, 10H), 1.39 (s, 9H), 2.32 (s, 3H), 3.75 (s, 3H), 7.24 (s, 1H), 7.31 (s, 1H)

$^{13}$C-NMR ($CDCl_3$, δ (ppm)): 6.96, 9.29, 21.07, 31.37, 35.07, 64.20, 127.41, 131.58, 132.72, 135.51, 141.89, 162.92

Example 2

Synthesis of (2-methoxy-3-tert-butyl-5-methylphenyl)(2,3,4,5-tetramethylcyclopentadien-1-yl)diethylsilane Under nitrogen atmosphere, 76 mL of THF was added to sodium hydride (60 wt %, 1.14 g, 47.42 mmol). A temperature of the tetrahydrofuran slurry of sodium hydride was raised to 50° C. Aniline (0.29 g, 3.16 mmol) was added, and the mixture was further stirred at 50° C. for 1 hour. A solution of 1,2,3,4-tetramethylcyclopentadiene (4.25 g, 34.78 mmol) in 19 mL of THF was slowly dropwise added thereto. After the completion of addition, the mixture was further stirred at 50° C. for 3 hours until the generation of a hydrogen gas ceased. After cooled to 20° C., a solution of (2-methoxy-3-tert-butyl-5-methylphenyl)chlorodimethylsilane (9.45 g, 31.61 mmol) in 19 mL of toluene was dropwise added, and stirring was continued at room temperature for 3 hours. The resultant reaction solution was dropwise added to a mixed solution obtained by cooling 47 mL of a 10% aqueous sodium bicarbonate solution and 47 mL of a 10% aqueous sodium carbonate solution at 0° C. to terminate the reaction, 47 mL of toluene was added, and the mixed solution was separated. After drying with sodium sulfate, concentration of the solution under reduced pressure afforded a mixture of (2-methoxy-3-tert-butyl-5-methylphenyl)(2,3,4,5-tetramethylcyclopentadien-1-yl)diethylsilane. (2-Methoxy-3-tert-butyl-5-methylphenyl)-(2,3,4,5-tetramethylcyclopentadien-1-yl) diethylsilane was purified by silica gel column chromatography.

$^1$H-NMR (toluene-$d_8$, δ (ppm)): 0.96-1.00 (m, 10H), 1.44 (s, 9H), 1.81 (s, 6H), 1.84 (s, 6H), 2.20 (s, 3H), 3.46 (s, 1H), 3.58 (s, 3H), 7.11 (s, 1H), 7.18 (s, 1H)

$^{13}$C-NMR (toluene-d$_8$, δ (ppm)): 4.62, 8.38, 11.38, 14.62, 21.21, 30.31, 31.41, 35.22, 129.92, 130.11, 131.91, 133.72, 135.90, 135.94, 141.88, 164.14

Example 3

Synthesis of [1-(diethyl{2-methoxy-3-tert-butyl-5-methylphenyl}silyl)-2,3,4,5-tetramethylcyclopentadienyl]bis(o-N,N-dimethylaminobenzyl)-scandium (hereinafter, referred to as scandium complex (1))

Synthesis of tris(o-N,N-dimethylaminobenzyl)scandium

Tris(o-N,N-dimethylaminobenzyl)scandium was synthesized according to the published article (J. Am. Chem. Soc. 1978, 100, 8068).
$^1$H-NMR (toluene-d$_8$, δ (ppm)): 1.58 (s, 6H), 2.28 (s, 18H), 6.71-6.78 (m, 6H), 6.85-6.95 (m, 6H)
Mass spectrum (EI-MS, m/z): 313 (M$^+$−134), 268, 134, 91, 65

Synthesis of Scandium Complex (1)

Under nitrogen atmosphere, tris(o-N,N-dimethylaminobenzyl)-scandium (0.50 g, 1.12 mmol) was dissolved in 6 mL of THF, and a mixture prepared by dissolving (2-methoxy-3-tert-butyl-5-methylphenyl)-(2,3,4,5-tetramethylcyclopentadien-1-yl)diethylsilane (0.43 g, 1.12 mmol) in 6 mL of tetrahydrofuran was added at room temperature. Stirring was continued at room temperature for 3 days. The mixture was concentrated under reduced pressure, and hexane was added to obtain scandium complex (1) (0.48 g, yield 61.4%) as a pale yellow solid.
$^1$H-NMR (toluene-d$_8$, δ (ppm)): 1.22-1.70 (m, 10H), 1.40 (s, 9H), 1.54 (s, 4H), 1.73 (s, 6H), 1.76 (s, 6H), 2.30 (s, 3H), 2.39 (s, 12H), 2.84 (s, 3H), 6.71-6.83 (m, 4H), 6.93-7.12 (m, 4H), 7.18 (s, 1H), 7.39 (s, 1H)
Mass spectrum (EI-MS, m/z): 384 (M$^+$−313), 355, 325, 235, 207, 177, 161, 117, 57

Example 4

Synthesis of [1-(diethyl{2-methoxy-3-tert-butyl-5-methyphenyl}silyl)-2,3,4,5-tetramethylcyclopentadienyl]bis(o-N,N-dimethylaminobenzyl)-lutetium (hereinafter, referred to as lutetium complex (1))

Synthesis of tris(o-N,N-dimethylaminobenzyl)lutetium

Tris(o-N,N-dimethylaminobenzyl)lutetium was synthesized in the same manner as that for the synthesis of tris(o-N,N-dimethylaminobenzyl)-scandium in Example 3 except that lutetium chloride was used.
$^1$H-NMR (toluene-d$_8$, δ (ppm)): 1.41 (s, 6H), 2.18 (s, 18H), 6.65-6.78 (m, 6H), 6.91-7.07 (m, 6H)
Mass spectrum (EI-MS, m/z): 443 (M$^+$−134), 268, 134, 120, 118, 91, 65

Synthesis of Lutetium Complex (1)

Under nitrogen atmosphere, tris(o-N,N-dimethylaminobenzyl)-lutetium (0.50 g, 1.04 mmol) was dissolved in 6 mL of tetrahydrofuran, and a mixture prepared by dissolving (2-methoxy-3-tert-butyl-5-methylphenyl)-(2,3,4,5-tetramethylcyclopentadien-1-yl)diethylsilane (0.40 g, 1.04 mmol) in 6 mL of tetrahydrofuran was added at room temperature. Stirring was continued at room temperature for 3 days, and the mixture was stirred at 60° C. for 6 hours. The mixture was concentrated under reduced pressure, and hexane was added to obtain lutetium complex (1) (0.51 g, yield 59.2%) as a white solid.
$^1$H-NMR (toluene-d$_8$, δ (ppm)): 1.23-1.65 (m, 10H), 1.35 (s, 4H), 1.40 (s, 9H), 1.83 (s, 12H), 2.27 (s, 3H), 2.32 (s, 12H), 2.88 (s, 3H), 6.66-6.80 (m, 4H), 6.94-7.15 (m, 4H), 7.19 (s, 1H), 7.43 (s, 1H)
Mass spectrum (EI-MS, m/z): 384 (M$^+$−443), 355, 325, 263, 235, 207, 179, 135, 120, 89, 57

Example 5

Synthesis of [1-{1-(2-methoxy-3-tert-butyl-5-methylphenyl)-1-methylethyl}-cyclopentadienyl]bis(o-N,N-dimethylaminobenzyl)yttrium (hereinafter, referred to as yttrium complex (1))

Synthesis of tris(o-N,N-dimethylaminobenzyl)yttrium

Tris(o-N,N-dimethylaminobenzyl)yttrium was synthesized in the same manner as that for the synthesis of tris(o-N,N-dimethylaminobenzyl)-scandium in Example 3 except that yttrium chloride was used.
$^1$H-NMR (toluene-d$_8$, δ (ppm)): 1.54 (s, 6H), 2.11 (s, 18H), 6.58-6.66 (m, 3H), 6.80-6.82 (m, 3H), 6.90-7.03 (m, 6H)
Mass spectrum (EI-MS, m/z): 357 (M$^+$−134), 268, 134, 120, 91, 65

Synthesis of 6-tert-butyl-2-[1-(cyclopentadienyl)-1-methylethyl]-1-methoxy-4-methylbenzene 6-Tert-butyl-2-[1-(cyclopentadienyl)-1-methylethyl]-1-methoxy-4-methylbenzene was synthesized according to the publication (JP-A-09-87313).

Synthesis of Yttrium Complex (1)

Under nitrogen atmosphere, tris(o-N,N-dimethylaminobenzyl)-yttrium (0.50 g, 1.02 mmol) was dissolved in 5 mL of tetrahydrofuran, and a mixture prepared by dissolving 6-tert-butyl-2-[1-(cyclopentadienyl)-1-methylethyl]-1-methoxy-4-methylbenzene (0.29 g, 1.02 mmol) in 5 mL of tetrahydrofuran was added at room temperature. After stirring was continued at room temperature for 24 hours, the mixture was concentrated under reduced pressure, and pentane was added to obtain yttrium complex (1) (0.34 g, yield 52.4%) as a white solid.
$^1$H-NMR (toluene-d$_8$, δ (ppm)): 1.45 (s, 13H), 1.90 (s, 6H), 2.25 (s, 15H), 3.01 (s, 3H), 5.58 (br s, 2H), 5.71-5.75 (m, 2H), 6.66-6.78 (m, 4H), 6.91-7.04 (m, 4H), 7.10 (br s, 2H)
Mass spectrum (EI-MS, m/z): 640 (M$^+$)

Example 6

Synthesis of [1-{1-(2-methoxy-3-tert-butyl-5-methylphenyl)-1-methylethyl}-cyclopentadienyl]bis(o-N,N-dimethylaminobenzyl)scandium (hereinafter, referred to as scandium complex (2))

Synthesis of Scandium Complex (2)

Under nitrogen atmosphere, tris(o-N,N-dimethylaminobenzyl)scandium (0.50 g, 1.12 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.32 g, 1.12 mmol) in 6 mL of tetrahydrofuran was added at room temperature. After stirring was continued at room temperature for 24 hours, the mixture was concentrated under reduced pressure, and pentane was added, followed by cooling to −20° C. The insolubles were filtered off, and the filtrate was cooled to −20° C. The resultant precipitate was washed with cold pentane to obtain scandium complex (2) (0.25 g, yield 37.3%) as a pale yellow solid.

$^1$H-NMR (toluene-d$_8$, δ (ppm)): 1.44 (s, 13H), 1.82 (s, 6H), 2.22 (s, 3H), 2.37 (s, 12H), 3.00 (s, 3H), 5.60 (br s, 2H), 5.70 (br s, 2H), 6.69-6.71 (m, 2H), 6.81-6.84 (m, 2H), 6.95-7.00 (m, 4H), 7.07-7.10 (m, 2H)

Mass spectrum (EI-MS, m/z): 596 (M$^+$)

Example 7

Synthesis of [1-{1-(2-methoxy-3-tert-butyl-5-methylphenyl)-1-methylethyl}-cyclopentadienyl]bis(o-N,N-dimethylaminobenzyl)lutetium (hereinafter, referred to as lutetium complex (2))

Synthesis of Lutetium Complex (2)

Under nitrogen atmosphere, tris(o-N,N-dimethylaminobenzyl)-lutetium (0.70 g, 1.21 mmol) was dissolved in 6 mL of tetrahydrofuran, and a mixture prepared by dissolving 6-tert-butyl-2-[1-(cyclopentadienyl)-1-methylethyl]-1-methoxy-4-methyl-benzene (0.34 g, 1.21 mmol) in 6 mL of tetrahydrofuran was added at room temperature. After stirring was continued at room temperature for 24 hours, the mixture was concentrated under reduced pressure, and pentane was added, followed by cooling to −20° C. The resultant precipitate was washed with cold pentane to obtain lutetium complex (2) (0.62 g, yield 70.5%) as a white solid.

$^1$H-NMR (toluene-d$_8$, δ (ppm)): 1.45 (s, 13H), 1.60-2.10 (br d, 6H), 2.24 (s, 3H), 2.20-2.47 (br s, 12H), 3.01 (s, 3H), 5.40-5.80 (br, 4H), 6.65-6.68 (m, 2H), 6.76-6.82 (m, 2H), 6.92-7.01 (m, 4H), 7.07-7.12 (m, 2H)

Mass spectrum (EI-MS, m/z): 726 (M$^+$)

Example 8

Synthesis of [1-{1-(2-methoxy-3-tert-butyl-5-methylphenyl)-1-methylethyl}-cyclopentadienyl]bis(o-N,N-dimethylaminobenzyl)thulium (hereinafter, referred to as thulium complex (1))

Synthesis of tris(o-N,N-dimethylaminobenzyl)thulium

Tris(o-N,N-dimethylaminobenzyl)thulium was synthesized in the same manner as that for the synthesis of tris(o-N,N-dimethylaminobenzyl)-scandium in Example 3 except that thulium chloride was used.

Mass spectrum (EI-MS, m/z): 571 (M$^+$), 437, 134, 120, 91, 65

Synthesis of Thulium Complex (1)

Under nitrogen atmosphere, tris(o-N,N-dimethylaminobenzyl)-thulium (0.70 g, 1.22 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.35 g, 1.22 mmol) in 6 mL of tetrahydrofuran was added at room temperature. After stirring was continued at room temperature for 24 hours, the mixture was concentrated under reduced pressure, and pentane was added, followed by cooling to −20° C. The resultant precipitate was washed with cold pentane to obtain thulium complex (1) (0.63 g, yield 71.8%) as a yellow solid.

Mass spectrum (EI-MS, m/z): 720 (M$^+$)

Example 9

Synthesis of [1-{1-(2-methoxy-3-tert-butyl-5-methylphenyl)-1-methylethyl}-cyclopentadienyl]bis(o-N,N-dimethylaminobenzyl)erbium (hereinafter, referred to as erbium complex (1))

Synthesis of tris(o-N,N-dimethylaminobenzyl)erbium

Tris(o-N,N-dimethylaminobenzyl)erbium was synthesized in the same manner as that for the synthesis of tris(o-N,N-dimethylaminobenzyl)-scandium in Example 3 except that erbium chloride was used.

Mass spectrum (EI-MS, m/z): 568 (M$^+$), 434, 134, 120, 91, 65

Synthesis of erbium complex (1)

Under nitrogen atmosphere, tris(o-N,N-dimethylaminobenzyl)-erbium (0.70 g, 1.23 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.35 g, 1.23 mmol) in 6 mL of tetrahydrofuran was added at room temperature. After stirring was continued at room temperature for 24 hours, the mixture was concentrated under reduced pressure, and pentane was added, followed by cooling to −20° C. The resultant precipitate was washed with cold pentane to obtain erbium complex (1) (0.65 g, yield 74.1%) as a pale pink solid.

Mass spectrum (EI-MS, m/z): 719 (M$^+$)

Example 10

Synthesis of [1-{1-(2-methoxy-3-tert-butyl-5-methylphenyl)-1-methylethyl}-cyclopentadienyl]bis(o-N,N-dimethylaminobenzyl)holmium (hereinafter, referred to as holmium complex (1))

Synthesis of tris(o-N,N-dimethylaminobenzyl)holmium

Tris(o-N,N-dimethylaminobenzyl)holmium was synthesized in the same manner as that for the synthesis of tris(o-N,N-dimethylaminobenzyl)-scandium in Example 3 except that holmium chloride was used.

Mass spectrum (EI-MS, m/z): 567 (M$^+$), 433, 135, 120, 91, 65

Synthesis of Holmium Complex (1)

Under nitrogen atmosphere, tris(o-N,N-dimethylaminobenzyl)-holmium (0.70 g, 1.23 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.35 g, 1.23 mmol) in 6 mL of tetrahydrofuran was added at room temperature. After stirring was continued at room temperature for 24 hours, the mixture was concentrated under reduced pressure, and pentane was added, followed by cooling to −20° C. The resultant precipitate was washed with cold pentane to obtain holmium complex (1) (0.61 g, yield 69.7%) as a pale orange solid.

Mass spectrum (EI-MS, m/z): 716 (M$^+$)

Example 11

Synthesis of [1-{1-(2-methoxy-3-tert-butyl-5-methylphenyl)-1-methylethyl}-cyclopentadienyl]bis(o-N,N-dimethylaminobenzyl)dysprosium (hereinafter, referred to as dysprosium complex (1))

Synthesis of tris(o-N,N-dimethylaminobenzyl)dysprosium

Tris(o-N,N-dimethylaminobenzyl)dysprosium was synthesized in the same manner as that for the synthesis of tris(o-N,N-dimethylaminobenzyl)-scandium in Example 3 except that dysprosium chloride was used.

Mass spectrum (EI-MS, m/z): 432 (M$^+$−133), 268, 135, 120, 65

Synthesis of Dysprosium Complex (1)

Under nitrogen atmosphere, tris(o-N,N-dimethylaminobenzyl)-dysprosium (0.70 g, 1.24 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.35 g, 1.24 mmol) in 6 mL of tetrahydrofuran was added at room temperature. After stirring was continued at room temperature for 24 hours, the mixture was concentrated under reduced pressure, and pentane was added, followed by cooling to −20° C. The resultant precipitate was washed with cold pentane to obtain dysprosium complex (1) (0.63 g, yield 71.6%) as a pale yellow solid.

Mass spectrum (EI-MS, m/z): 714 (M$^+$)

Example 12

Synthesis of [1-{1-(2-methoxy-3-tert-butyl-5-methylphenyl)-1-methylethyl}-cyclopentadienyl]bis(o-N,N-dimethylaminobenzyl)terbium (hereinafter, referred to as terbium complex (1))

Synthesis of tris(o-N,N-dimethylaminobenzyl)terbium

Tris(o-N,N-dimethylaminobenzyl)terbium was synthesized in the same manner as that for the synthesis of tris(o-N,N-dimethylaminobenzyl)-scandium in Example 3 except that dysprosium chloride was used.

Mass spectrum (EI-MS, m/z): 427 (M$^+$−134), 268, 135, 120, 91, 65

Synthesis of Terbium Complex (1)

Under nitrogen atmosphere, tris(o-N,N-dimethylaminobenzyl)-terbium (0.70 g, 1.25 mmol) was dissolved in 6 mL of tetrahydrofuran, and a mixture prepared by dissolving 6-tert-butyl-2-[1-(cyclopentadienyl)-1-methylethyl]-1-methoxy-4-methylbenzene (0.35 g, 1.25 mmol) in 6 mL of tetrahydrofuran was added at room temperature. After stirring was continued at room temperature for 24 hours, the mixture was concentrated under reduced pressure, and pentane was added to remove the insolubles by filtration. The filtrate was cooled to −20° C. The resultant precipitate was washed with cold pentane to obtain terbium complex (1) (0.56 g, yield 62.5%) as a yellow solid.

Mass spectrum (EI-MS, m/z): 710 (M$^+$)

Production of ethylene-α-olefin copolymer

Physical properties were measured by the following method.

(1) 1-Hexene Unit Content in Copolymer (SCB, Unit: 1/1000 C)

Using an infrared spectrophotometer (EQUINOX 55 manufactured by Bruker), the unit content was obtained by infrared spectroscopy. The characteristic absorption of butyl branches was expressed using a peak in a range of 1378 cm$^{-1}$ to 1303 cm$^{-1}$, and a 1-hexene unit content was expressed as the number of butyl branches per 1000 carbon atoms of an ethylene-1-hexene copolymer.

(2) Molecular Weight and Molecular Weight Distribution

A molecular weight and a molecular weight distribution were measured by gel permeation chromatography (GPC) under the following conditions. The molecular weight distribution was assessed by a ratio (Mw/Mn) of a weight average molecular weight (Mw) to a number average molecular weight (Mn).

Apparatus: Pump apparatus (LC pump) Model 305 (pump head 25.SC) manufactured by Gilson Column: PLgel Mixed-B 10 μm (7.5 mmφ×300 mm) manufactured by Polymer Laboratories Measurement temperature: 160° C.

Mobile phase: Orthodichlorobenzene

Sample concentration: Copolymer 1 mg/1,2,4-trichlorobenzene 1 mL

Flow rate: 2 mL/min.

Standard materials: (Standard polystyrene molecular weight) 5,000, 10,050, 28,500, 65,500, 185, 400, 483,000, 1,013,000, 3,390,000

Ethylene and 1-hexene was copolymerized in the presence of scandium complex (1) obtained in Example 3 as a catalytic component for olefin polymerization using PPR (equipped with 48 autoclaves) manufactured by Symyx under the polymerization conditions described below.

Example 13

Under nitrogen atmosphere, 5.0 mL of toluene and 60 μL of 1-hexene were charged in an autoclave and stabilized at 40° C. Then, ethylene was pressurized to 0.60 MPa and stabilized. To this mixture, 100 μmol (in terms of Al atoms) of aluminoxane (MMAO manufactured by Tosoh Finechem Corporation, 5.8 wt % Al) and 0.10 μmol of scandium complex (1) were added, and polymerization was performed for 30 minutes. As the result of polymerization, a polymer having a molecular weight (Mw) of 676,000, a molecular weight distribution (Mw/Mn) of 11.2, a 1-hexene unit content in a copolymer (SCB) of 10 was produced at a rate 1.9×10$^6$ g per 1 mol of a catalyst per 1 hour.

Example 14

Polymerization was performed in the same manner as in Example 13 except that the amount of 1-hexene was changed to 50 μL, and a polymerization temperature was changed to 70° C., to produce a polymer having a molecular weight (Mw) of 262,000, a molecular weight distribution (Mw/Mn) of 9.0, and a 1-hexene content in a copolymer (SCB) of 8 at a rate of $6.9 \times 10^6$ g per 1 mol of a catalyst per 1 hour.

Example 15

Polymerization was performed in the same manner as in Example 13 except that the amount of 1-hexene was changed to 40 μL, a polymerization temperature was changed to 130° C., and the amount of aluminoxane was changed to 10 μmol, to produce a polymer having a molecular weight (Mw) of 59,000, a molecular weight distribution (Mw/Mn) of 1.6, and a 1-hexene content in a copolymer (SCB) of 1 at a rate of $20.5 \times 10^6$ g per 1 mol of a catalyst per 1 hour.

Example 16

Under nitrogen atmosphere, 5.0 mL of toluene and 60 μL of 1-hexene were charged in an autoclave and stabilized at 40° C. Then, ethylene was pressurized to 0.60 MPa and stabilized. To this mixture, 40 μL of a hexane solution of triisobutylaluminum (hereinafter, referred to as TIBA (manufactured by Kanto Chemical Co., Inc., TIBA concentration 1.0 mol/L), 0.30 μmol of tris(pentafluorophenyl)borane, and 0.10 μmol of scandium complex (1) were added, and polymerization was performed for 30 minutes. As the result of polymerization, a polymer having a molecular weight (Mw) of 1,867,000, a molecular weight distribution (Mw/Mn) of 1.8, and a 1-hexene content in a copolymer (SCB) of 6 was produced at a rate of $1.5 \times 10^6$ g per 1 mol of a catalyst per 1 hour.

Example 17

Under nitrogen atmosphere, 5.0 mL of toluene and 60 μL of 1-hexene were charged in an autoclave and stabilized at 40° C. Then, ethylene was pressurized to 0.60 MPa and stabilized. To this mixture, 40 μL of a hexane solution of TIBA (manufactured by Kanto Chemical Co., Inc., TIBA concentration 1.0 mol/L), 0.30 μmol of dimethylanilinium tetrakis(pentafluorophenyl)borate, and 0.10 μmol of scandium complex (1) were added, and polymerization was performed for 30 minutes. As the result of polymerization, a polymer having a molecular weight (Mw) of 144,000, a molecular weight distribution (Mw/Mn) of 1.8, and a 1-hexene content in a copolymer (SCB) of 1 was produced at a rate of $44.2 \times 10^6$ g per 1 mol of a catalyst per 1 hour.

Example 18

Polymerization was performed in the same manner as in Example 17 except that the amount of 1-hexene was changed to 50 μL, and a polymerization temperature was changed to 70° C., to produce a polymer having a molecular weight (Mw) of 54,000, a molecular weight distribution (Mw/Mn) of 1.7, and a 1-hexene content in a copolymer (SCB) of 30 at a rate of $205.0 \times 10^6$ g per 1 mol of a catalyst per 1 hour.

Example 19

Polymerization was performed in the same manner as in Example 17 except that the amount of 1-hexene was changed to 40 μL, a polymerization temperature was changed to 130° C., and the amount of a hexane solution of TIBA was changed to 4 μL, to produce a polymer at a rate of $2.7 \times 10^6$ g per 1 mol of a catalyst per 1 hour.

Example 20

Under nitrogen atmosphere, 5.0 mL of toluene and 60 μL of 1-hexene were charged in an autoclave and stabilized at 40° C. Then, ethylene was pressurized to 0.60 MPa and stabilized. To this mixture, 40 μL of a hexane solution of TIBA (manufactured by Kanto Chemical Co., Inc., TIBA concentration 1.0 mol/L), 0.30 μmol of triphenylmethyl tetrakis(pentafluorophenyl)borate, and 0.10 μmol of scandium complex (1) were added, and polymerization was performed for 30 minutes. As the result of polymerization, a polymer having a molecular weight (Mw) of 230,000, a molecular weight distribution (Mw/Mn) of 1.9, and a 1-hexene content in a copolymer (SCB) of 5 was produced at a rate of $87.6 \times 10^6$ g per 1 mol of a catalyst per 1 hour.

Example 21

Polymerization was performed in the same manner as in Example 20 except that the amount of 1-hexene was changed to 50 μL, and a polymerization temperature was changed to 70° C., to produce a polymer having a molecular weight (Mw) of 98,000, a molecular weight distribution (Mw/Mn) of 1.7, and a 1-hexene content in a copolymer (SCB) of 36 at a rate of $175.3 \times 10^6$ g per 1 mol of a catalyst per 1 hour.

Example 22

Polymerization was performed in the same manner as in Example 20 except that the amount of 1-hexene was changed to 40 μL, a polymerization temperature was changed to 130° C., and the amount of a hexane solution of TIBA was changed to 4 μL, to produce a polymer at a rate of $1.4 \times 10^6$ g per 1 mol of a catalyst per 1 hour.

Example 23

Under nitrogen atmosphere, 5.0 mL of toluene and 50 μL of 1-hexene were charged in an autoclave and stabilized at 70° C. Then, ethylene was pressurized to 0.60 MPa and stabilized. To this mixture, 0.30 μmol of triphenylmethyl tetrakis(pentafluorophenyl)borate, and 0.10 μmol of scandium complex (1) were added, and polymerization was performed for 30 minutes. As the result of polymerization, a polymer having a molecular weight (Mw) of 1,527,000, a molecular weight distribution (Mw/Mn) of 1.4, and a 1-hexene content in a copolymer (SCB) of 199 was produced at a rate of $14.5 \times 10^6$ g per 1 mol of a catalyst per 1 hour.

Production of Ethylene Homopolymer

Ethylene was homopolymerized in the presence of scandium complex (1) obtained in Example 3 as a catalytic component for olefin polymerization using PPR (equipped with 48 autoclaves) manufactured by Symyx, under the polymerization conditions described below.

Example 24

Under nitrogen atmosphere, 5.0 mL of toluene was charged in an autoclave and stabilized at 40° C. Then, ethylene was pressurized to 0.60 MPa and stabilized. To this mixture, 100 μmol (in terms of Al atom) of aluminoxane (MMAO manufactured by Tosoh Finechem Corporation, 5.8 wt % Al), and 0.10 μmol of scandium complex (1) were added, and polymerization was performed for 30 minutes. As the result of polymerization, a polymer was produced at a rate of $1.3 \times 10^5$ g per 1 mol of a catalyst per 1 hour.

Example 25

Polymerization was performed in the same manner as in Example 24 except that 40 μL of a hexane solution of TIBA (manufactured by Kanto Chemical Co., Inc., TIBA concentration 1.0 mol/L) and 0.30 μmol of tris(pentafluorophenyl) borane were used in place of methylaluminoxane. As the result of polymerization, a polymer was produced at a rate of $1.1 \times 10^5$ g per 1 mol of a catalyst per 1 hour.

Example 26

Polymerization was performed in the same manner as in Example 24 except that 40 μL of a hexane solution of TIBA (manufactured by Kanto Chemical Co., Inc., TIBA concentration 1.0 mol/L) and 0.30 μmol of dimethylanilinium tetrakis(pentafluorophenyl)borate were used in place of methylaluminoxane. As the result of polymerization, a polymer was produced at a rate of $24.2 \times 10^6$ g per 1 mol of a catalyst per 1 hour.

Example 27

Polymerization was performed in the same manner as in Example 24 except that 40 μL of a hexane solution of TIBA (manufactured by Kanto Chemical Co., Inc., TIBA concentration 1.0 mol/L) and 0.30 μmol of triphenylmethyl tetrakis (pentafluorophenyl)borate were used in place of methylaluminoxane. As the result of polymerization, a polymer was produced at a rate of $30.3 \times 10^6$ g per 1 mol of a catalyst per 1 hour.

Example 28

Polymerization was performed in the same manner as in Example 24 except that 0.30 μmol of triphenylmethyl tetrakis (pentafluorophenyl)borate was used in place of methylaluminoxane. As the result of polymerization, a polymer was produced at a rate of $9.0 \times 10^5$ g per 1 mol of a catalyst per 1 hour.

Ethylene and 1-hexene were copolymerized in the presence of lutetium complex (1) obtained in Example 4 as a catalytic component for olefin polymerization using PPR (equipped with 48 autoclaves) manufactured by Symyx under the polymerization conditions described below.

Example 29

Under nitrogen atmosphere, 5.0 mL of toluene and 50 μL of 1-hexene were charged in an autoclave and stabilized at 70° C. Then, ethylene was pressurized to 0.60 MPa and stabilized. To this mixture, were added 40 μL of a hexane solution of TIBA (manufactured by Kanto Chemical Co., Inc., TIBA concentration 1.0 mol/L), 0.30 μmol of dimethylanilinium tetrakis(pentafluorophenyl)borate, and 0.10 μmol of lutetium complex (1) were added, and polymerization was performed for 30 minutes. As the result of polymerization, a polymer having a molecular weight (Mw) of 508,000, a molecular weight distribution (Mw/Mn) of 22.7, and a 1-hexene content in a copolymer (SCB) of 49 was produced at a rate of $1.6 \times 10^6$ g per 1 mol of a catalyst per 1 hour.

<Process for Producing Polymer of Polar Monomer>
<Process for Producing Lactone Polymer>

A molecular weight and a molecular weight distribution were measured by gel permeation chromatography (GPC) according to the following method.

Apparatus: HLC-8120GPC (RI)

Column: TSKgel, GMH HR-M

Flow rate: 0.5 mL/min

Measurement temperature: 40° C.

Mobile phase: THF

Standard material: Polystyrene

Example 30

Under nitrogen atmosphere, all the amount of a toluene solution (2 mL) of scandium complex (2) (37.6 mg, 0.063 mmol) was added at once to ε-caprolactone (2.87 g, 25.2 mmol) while vigorously stirring with a magnetic stirrer at room temperature. One (1) minute after addition, methanol (100 mL) was added to terminate polymerization, and the resultant white solid was collected by filtration. Vacuum drying at 60° C. afforded polycaprolactone (2.84 g, yield 99%). The resultant polycaprolactone was subjected to GPC analysis to find that a weight average molecular weight Mw (in terms of polystyrene) was 56,700, and a molecular weight distribution Mw/Mn was 1.39.

Example 31

Under nitrogen atmosphere, all the amount of a toluene solution (4 mL) of scandium complex (2) (38.5 mg, 0.065 mmol) was added at once to ε-caprolactone (5.75 g, 50.4 mmol) while vigorously stirring with a magnetic stirrer at room temperature. Three (3) minutes after addition, methanol (100 mL) was added to terminate polymerization, and the resultant white solid was collected by filtration. Vacuum drying at 60° C. afforded polycaprolactone (5.04 g, yield 88%). The resultant polycaprolactone was subjected to GPC analysis to find that a weight average molecular weight Mw (in terms of polystyrene) was 113,000, and a molecular weight distribution Mw/Mn was 1.58.

Example 32

Under nitrogen atmosphere, all the amount of a toluene solution (2 mL) of scandium complex (1) (43.9 mg, 0.063 mmol) was added at once to ε-caprolactone (2.88 g, 25.2 mmol) while vigorously stirring with a magnetic stirrer at room temperature. One (1) minute after addition, methanol (100 mL) was added to terminate polymerization, and the resultant white solid was collected by filtration. Vacuum drying at 60° C. afforded polycaprolactone (2.73 g, yield 95%). The resultant polycaprolactone was subjected to GPC analysis to find that a weight average molecular weight Mw was 49,400, and a molecular weight distribution Mw/Mn was 1.77.

Example 33

Under nitrogen atmosphere, all the amount of a toluene solution (2 mL) of yttrium complex (1) (41.0 mg, 0.064 mmol) was added at once to ε-caprolactone (2.87 g, 25.2 mmol) while vigorously stirring with a magnetic stirrer at room temperature. Fifteen (15) seconds after addition, methanol (100 mL) was added to terminate polymerization, and the resultant white solid was collected by filtration. Vacuum drying at 60° C. afforded polycaprolactone (2.79 g, yield 97%). The resultant polycaprolactone was subjected to GPC analysis to find that a weight average molecular weight Mw (in terms of polystyrene) was 41,900, and a molecular weight distribution Mw/Mn was 1.88.

Example 34

Under nitrogen atmosphere, all the amount of a toluene solution (2 mL) of lutetium complex (2) (45.8 mg, 0.063 mmol) was added at once to ε-caprolactone (2.88 g, 25.2 mmol) while vigorously stirring with a magnetic stirrer at room temperature. Ten (10) seconds after addition, methanol (100 mL) was added to terminate polymerization, and the resultant white solid was collected by filtration. Vacuum drying at 60° C. afforded polycaprolactone (2.79 g, yield 97%). The resultant polycaprolactone was subjected to GPC analysis to find that a weight average molecular weight Mw (in terms of polystyrene) was 57,700, and a molecular weight distribution Mw/Mn was 2.23.

<Process for Producing Alkylene Oxide Polymer>

A molecular weight and a molecular weight distribution were measured by gel permeation chromatography (GPC) according to the following method.

Apparatus: HLC-8120GPC (RI)

Column: TSKgel, GMH HR-M

Flow rate: 0.5 mL/min

Measurement temperature: 40° C.

Mobile phase: THF

Standard material: Polystyrene

Polymerization of cyclohexene oxide

Example 35

Under nitrogen atmosphere, scandium complex (2) (44.3 mg, 0.06 mmol) was added to cyclohexene oxide (2.47 g, 25.20 mmol) while stirring at room temperature to thereby initiate polymerization. Polymerization was performed at room temperature for 30 minutes, and methanol (100 mL) was added to terminate polymerization, and a polymer was obtained by filtration. The resultant polymer was vacuum-dried (50° C., 3 hours) to obtain poly(cyclohexene oxide) as a white solid (1.64 g, yield 66%). The resultant poly(cyclohexene oxide) had a weight average molecular weight Mw (in terms of polystyrene) of 495,000, and an Mw/Mn of 2.06.

Example 36

Under nitrogen atmosphere, all the amount of a catalyst solution obtained by dissolving scandium complex (2) (37.6 mg, 0.06 mmol) in toluene (2 mL) was added at once to cyclohexene oxide (2.47 g, 25.20 mmol) while stirring at room temperature to thereby initiate polymerization. Polymerization was performed at room temperature for 6 hours, methanol (100 mL) was added to terminate polymerization, and a polymer was obtained by filtration. The resultant polymer was vacuum-dried (60° C., 3 hours) to obtain poly(cyclohexene oxide) as a white solid (0.34 g, yield 14%). The resultant poly(cyclohexene oxide) had a weight average molecular weight Mw (in terms of polystyrene) of 436,000, and an Mw/Mn of 2.01.

Example 37

Under nitrogen atmosphere, all the amount of a catalyst solution obtained by dissolving scandium complex (1) (37.6 mg, 0.06 mmol) in toluene (2 mL) was added at once to cyclohexene oxide (2.47 g, 25.20 mmol) while stirring at room temperature to thereby initiate polymerization. Polymerization was performed at room temperature for 6 hours, methanol (100 mL) was added to terminate polymerization, and a polymer was obtained by filtration. The resultant polymer was vacuum-dried (60° C., 3 hours) to obtain poly(cyclohexene oxide) as a white solid (0.21 g, yield 9%). The resultant poly(cyclohexene oxide) had a weight average molecular weight Mw (in terms of polystyrene) of 207,000, and an Mw/Mn of 1.54.

<Process for Producing (Meth)Acrylate Ester Polymer>

Tactility was measured by proton nuclear magnetic resonance spectrum ($^1$H-NMR) according to the published article (e.g. Organometallics 2007, 26, 187-195).

Apparatus: EX270 manufactured by JEOL Ltd., or DPX-300 manufactured by Bruker

Sample cell: 5 mmφ tube

Measurement solvent: $CDCl_3$

Sample concentration: 30 mg/0.5 mL ($CDCl_3$)

Measurement temperature: room temperature (about 25° C.)

Measurement parameter: 5 mmφ probe, MENUF NON, OBNUC $^1$H,

Accumulation times 16

Pulse angle: 45 degrees

Repetition time: ACQTM 3 seconds, PD 4 seconds

Internal standard: $CDCl_3$ (7.26 ppm)

Example 38

Polymerization of Methyl Methacrylate

Under nitrogen atmosphere, all the amount of a catalyst solution obtained by dissolving scandium complex (2) (37.6 mg, 0.06 mmol) in toluene (2 mL) was added at once to methyl methacrylate (2.52 g, 25.20 mmol) while stirring at room temperature to thereby initiate polymerization. Polymerization was performed at room temperature for 6 hours, methanol (100 mL) was added to terminate polymerization, and a polymer was obtained by filtration. The resultant polymer was vacuum-dried (80° C., 3 hours) to obtain poly(methyl methacrylate) as a white solid (0.26 g, yield 11%). The resultant poly(methyl methacrylate) had a weight average molecular weight Mw (in terms of polystyrene) of 72,000, an Mw/Mn of 2.13, and a stereoregularity rr/mr/mm of 73.0/22.8/4.2.

The invention claimed is:

1. A rare earth metal complex represented by the formula (1):

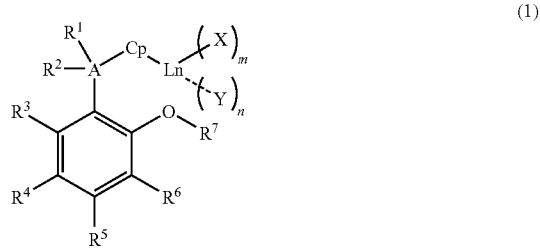

wherein

A represents a Group 14 element of the periodic table,

Cp represents a group having a substituted or unsubstituted cyclopentadienyl anion moiety, Ln represents a Group 3 metal atom or a lanthanoid metal atom, $R^1$, $R^2$, $R^3$, $R^4$, $R^5$ and $R^6$ are the same or different, and represent a hydrogen atom, a halogen atom, an alkyl group having 1 to 20 carbon atoms, an aryl group having 6 to 20 carbon atoms, an aralkyl group having 7 to 20 carbon atoms, a silyl group substituted with a hydrocarbon group having 1 to 20 carbon atoms, an alkoxy group having 1 to 20 carbon atoms, an aryloxy group having 6 to 20 carbon atoms, an aralkyloxy group having 7 to 20 carbon atoms, or an amino group substituted with a hydrocarbon group having 1 to 20 carbon atoms, $R^7$ represents an alkyl group having 1 to 20 carbon atoms, an aryl group having 6 to 20 carbon atoms, or an aralkyl group having 7 to 20 carbon atoms, Provided that, in $R^1$ to $R^7$, the alkyl group, the aryl group, the aralkyl group, the alkoxy group, the aryloxy group, the arylkyloxy group or the hydrocarbon group may be substituted with a halogen atom, $R^1$ and $R^2$ may be bonded together to form a ring, adjacent groups of $R^3$, $R^4$, $R^5$ and $R^6$ may optionally be bonded together to form a ring, respectively, m Xs are the same or different, and represent a monoanionic ligand, n Ys are the same or different, and represent a neutral ligand, m represents an integer of 1 to 3, and n represents an integer of 0 to 3.

2. The rare earth metal complex according to claim 1, wherein A is a silicon atom.

3. The rare earth metal complex according to claim 1, wherein Ln is scandium, yttrium, terbium, dysprosium, holmium, erbium, thulium or lutetium.

4. A process for producing the rare earth metal complex as claimed in claim 1 comprising the step of reacting a substituted or unsubstituted cyclopentadiene compound represented by the formula (2):

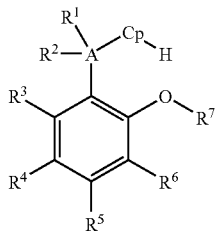

(2)

wherein A, Cp, $R^1$, $R^2$, $R^3$, $R^4$, $R^5$, $R^6$ and $R^7$ are the same as defined in claim 1 with a rare earth metal compound represented by the formula (3):

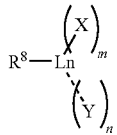

wherein Ln, X, Y, m and n are the same as defined in claim 1, $R^8$ represents an alkyl group optionally substituted with a silyl group substituted with a hydrocarbon group having 1 to 20 carbon atoms, or an aralkyl group optionally substituted with an amino group substituted with a hydrocarbon group having 1 to 20 carbon atoms.

5. A catalytic component for olefin polymerization comprising the rare earth metal complex as claimed in claim 1.

6. A catalyst for olefin polymerization, obtained by contacting the catalytic component for olefin polymerization as claimed in claim 5, with at least one compound selected from the group consisting of the following aluminum compounds (A1) to (A3) and the following boron compounds (B1) to (B3):

Aluminum compounds (A):

(A1): an organoaluminum compound represented by the formula:

$$(E^1)_a AlZ_{(3-a)};$$

(A2): a cyclic aluminoxane having a structure represented by the formula:

$$\{-Al(E^2)-O-\}_b; \text{ and}$$

(A3): a linear aluminoxane having a structure represented by the formula:

$$E^3\{-Al(E^3)-O-\}_c Al(E^3)_2$$

wherein a represents a number satisfying $0 < a \leq 3$, b represents an integer of at least 2, c represents an integer of at least 1, $E^1$, $E^2$ and $E^3$ each represent a hydrocarbon group having 1 to 20 carbon atoms, plural $E^1$s, plural $E^2$s and plural $E^3$s may be the same or different, Z represents a hydrogen atom or a halogen atom, and plural Zs may be the same or different); and Boron compounds (B):

(B1): a boron compound represented by the formula:

$$BQ^1Q^2Q^3;$$

(B2): a boron compound represented by the formula:

$$G^+(BQ^1Q^2Q^3Q^4)^-; \text{ and}$$

(B3): a boron compound represented by the formula:

$$(L^1-H)^+(BQ^1Q^2Q^3Q^4)^-$$

wherein B represents a boron atom in the trivalent state, $Q^1$, $Q^2$, $Q^3$ and $Q^4$ each represent independently a halogen atom, a hydrocarbon group, a halogenated hydrocarbon group, a substituted silyl group, an alkoxy group or a disubstituted amino group, $G^+$ represents an inorganic or organic cation, and $L^1$ represents a neutral Lewis base.

7. A process for producing an olefin polymer comprising the step of polymerizing an olefin in the presence of a catalyst for olefin polymerization as claimed in claim 6.

8. A process for producing an ethylene-α-olefin copolymer comprising the step of copolymerizing ethylene and α-olefin in the presence of a catalyst for olefin polymerization as claimed in claim 6.

9. A process for producing a polymer of a polar monomer comprising the step of contacting a polar monomer with a rare earth metal complex represented by the formula (1) as claimed in claim 1 to polymerize the monomer.

10. A process for producing a polymer of a lactone comprising contacting a lactone with a rare earth metal complex represented by the formula (1) as claimed in claim 1 to ring-opening polymerizing the lactones.

11. A process for producing a polymer of an alkylene oxide comprising the step of contacting an alkylene oxide with the rare earth metal complex represented by the formula (1) as claimed in claim 1 to ring-opening polymerize the alkylene oxides.

12. A process for producing an acrylate ester polymer or a methacrylate ester polymer comprising contacting an acrylate ester or a methacrylate ester with the rare earth metal complex represented by the formula (1) as claimed in claim 1 to polymerize the ester.

* * * * *